United States Patent
Akiyama et al.

(10) Patent No.: US 6,956,077 B1
(45) Date of Patent: Oct. 18, 2005

(54) TEMPERATURE-RESPONSIVE POLYMER COMPOUND AND PROCESS FOR PRODUCING THE SAME

(75) Inventors: Yoshikatsu Akiyama, Tokyo (JP); Kimihiro Yoshizako, Ibaraki (JP); Yukio Hasegawa, Chiba (JP); Teruo Okano, Ichikawa (JP)

(73) Assignee: Amersham Biosciences KK, Tokyo (JP)

( * ) Notice: Subject to any disclaimer, the term of this patent is extended or adjusted under 35 U.S.C. 154(b) by 0 days.

(21) Appl. No.: 09/890,447

(22) PCT Filed: Jan. 31, 2000

(86) PCT No.: PCT/JP00/00510

§ 371 (c)(1),
(2), (4) Date: Oct. 19, 2001

(87) PCT Pub. No.: WO00/07002

PCT Pub. Date: Feb. 10, 2000

(30) Foreign Application Priority Data

| Jan. 29, 1999 | (JP) | 11-023245 |
| Jan. 29, 1999 | (JP) | 11-023246 |
| May 7, 1999 | (JP) | 11-127211 |
| Jun. 8, 1999 | (JP) | 11-161372 |
| Jun. 9, 1999 | (JP) | 11-162486 |

(51) Int. Cl.[7] .................. C08K 5/16; C12N 11/08; A61K 31/74
(52) U.S. Cl. .................. 524/330.3; 435/174; 435/180; 424/78.08; 424/78.17; 424/78.2
(58) Field of Search ............. 435/174, 180; 526/303.1, 304, 306, 330.3; 424/78.08, 78.2, 424/78.17

(56) References Cited

U.S. PATENT DOCUMENTS

| 2,458,420 A | 1/1949 | Eastman |
| 3,721,565 A | 3/1973 | Fitzgerald |
| 3,969,436 A | 7/1976 | Wichterle et al. |
| 4,062,831 A | 12/1977 | Kopecek et al. |
| 5,300,537 A * | 4/1994 | Muller et al. ............... 523/115 |

FOREIGN PATENT DOCUMENTS

| EP | 0 394 787 A | 10/1990 |
| EP | 0501301 A2 * | 2/1992 |
| EP | 0 697 400 A | 2/1996 |
| EP | 0 970 945 A1 | 1/2000 |
| GB | 1 409 967 A | 10/1975 |
| WO | WO 00/07002 A | 2/2000 |

OTHER PUBLICATIONS

Yakovleva, M., et al. "Radiation Polymerization of Acrylamide in Two-Phase Systems" Chemical Abstracts, vol. 79, vol. 79, No. 22, Dec. 3, 1973, Columbus, Ohio, US; abstract No. 126818 XP002137858 abstracts & Radiats. Khim. (1972), 2, 251-7 from: Ref. Zh., Khim. 1973, Abstr. No. 3S154.

(Continued)

*Primary Examiner*—Jean C. Witz
*Assistant Examiner*—Susan Hanley
(74) *Attorney, Agent, or Firm*—Royal N. Ronning, Jr.; Stephen G. Ryan; Yonggang Ji

(57) ABSTRACT

A temperature-responsive polymer and polymer material which has ester bond(s) and/or acid amide bond(s) respectively at one or more sites in the side chain and can be arbitrarily controlled by varying the side chain is provided.

3 Claims, 15 Drawing Sheets

OTHER PUBLICATIONS

Database WPI, Section Ch. Week 199440, Derwent Publications Ltd., London, GB; AN 1994-322147 XP002137859 and JP 06 247917 A (Nippon Shokubai Co. Ltd.) Sep. 6, 1994 Abstract.

Ogata, n., "Applications of Temperature-Responsive Polymers for Drug Delivery Systems" Chemical Abstracts, vol. 125, No. 20, Nov. 11, 1996, Columbus, Ohio, US, abstract No. 256962 XP002137584 abstract & Polym. Prepr. (Am. Chem. Soc., Div. Polym. Chem.) (1996), 37(2), 113-114.

Micewicz, B., et al. "Mechanism of Tyrosine Fluorescence Quenching by Acrylamide in Model Peptides" Pept. 1996, Proc. Eur. Pept. Symp., 24th (1998), Meeting Date 1996, 649-650, Editor(s): Ramage, R. and Epton, R. Publisher: Mayflower Scientific, Kingswinford, UK. XP000907133.

* cited by examiner

A: (acrylamide : 3-acrylamide acetanilide) = (90:10, mol/mol)

B: (acrylamide : 3-acrylamide acetanilide) = (85:15, mol/mol)

A: Aqueous solution
B: 300 mM aqueous solution of sodium chloride

TEMPERATURE-RESPONSIVE POLYMER COMPOUND AND PROCESS FOR PRODUCING THE SAME

TECHNICAL FIELD

This invention relates to a novel polymer compound which undergoes stretching and cohesion with a change in the polarity of the polymer per se due to a temperature change, a process for producing this polymer compound, a heat-responsive polymer material containing this compound, a separation method with the use of a material containing this heat-responsive polymer material, and a method for separating chemicals, biological polymers (proteins, peptides, etc.) and biological samples (cells, etc.) by using this material.

In addition, this invention relates to a temperature-responsive polymer compound a change in the characteristics of which can be controlled depending on temperature. Furthermore, the present invention relates to a temperature-responsive polymer compound which is usable, by taking advantage of the temperature-depending change in the characteristics thereof, in adsorption and separation materials, drug carriers, dielectric and magnetic materials, piezoelectric and pyroelectric materials, degradable and reactive materials, biofunctional materials, etc.

This invention also relates to a temperature-responsive polymer compound by which the polarity and hydrogen-bonding ability of a material can be changed or controlled depending on temperature. The present invention further relates to a temperature-responsive polymer compound which is usable in materials for adsorbing, separating and releasing substances to be applied to biological functions with the use of a change in the polarity and the hydrogen-bonding ability depending on temperature. The present invention furthermore relates to a method for adsorbing, separating, recovering and releasing substances characterized by using these polymer compounds.

It should be noted that the terms "heat-responsive" and "temperature-responsive" used herein have the same meaning.

BACKGROUND ART

Typical examples of heat-responsive polymer materials having ester bonds or acid amide bonds include partially oxidized polyvinyl alcohol and N-isopropyl acrylamides. It is known that the cloud point of an ester bond-type polymer or an alkylamide polymer would be gradually lowered with an increase in the carbon atom number in a side chain. It is therefore impossible to synthesize a heat-responsive polymer of the alkylamide type having a side chain with a large carbon atom number. In the case of an ester-bond type polymer or an alkylamide polymer, it is also difficult to provide a sufficient polarity in separating any protein.

N-Alkylacrylamides typified by N-isopropylacrylamide, which in polymer form are known to be temperature-responsive, have been frequently applied to DDS (Drug Delivery System) and separating agents. However, alkylacrylamide monomers showing temperature-responsiveness in polymer form carry exclusively alkyl groups with a small number of carbon atoms. Owing to this characteristic, these alkylacrylamides are poor in the hydrophobic nature or the hydrogen bonding properties, which makes it difficult to efficiently separate, adsorb and release all biological components or organic matters by using the these kinds of polymers. Although hydrogen-bonding groups can be introduced into these compounds by forming a copolymer with the use of a monomer having a hydrogen-bonding group, there arises a problem in this case, i.e., an increase in the cloud point or the disappearance of the temperature-responsiveness. As a result, a target substance, in particular, a biological component should be separated, adsorbed and released under severe conditions.

In polymer compounds showing structural changes due to external stimuli (temperature, pH, light, etc.), the structural changes result in changes in the characteristics of the polymers, for example, volume or hydrophilic/hydrophobic nature. For example, it is well known that poly(N-isopropyl acrylamide) shows a structural change in an aqueous solution depending on temperature. Namely, this compound is soluble in water in a low temperature side of 32° C. or below but becomes insoluble in water in a high temperature side exceeding 32° C. That is to say, it is a temperature-responsive polymer compound having a lower critical solution temperature (LCST). It is considered that such a polymer compound would show a hydrophilic nature and be dissolved in water in a swollen state in the low temperature side and, in the high temperature side, it would show a hydrophobic nature and be aggregated in a contracted state. By using these temperature-depending changes, temperature-responsive polymer compounds have been applied to drug delivery systems and high-functional materials such as separators.

To apply these temperature-responsive polymer compounds to high-functional materials, it is needed to use not only temperature-responsive polymer compounds having LCST but also those having the upper limit critical solution temperature (UCST), i.e., being insoluble in water in a low temperature side but becoming soluble in water in a high temperature side. When a protein unstable to heat is to be separated by adsorbing on a temperature-responsive polymer compound via a hydrophobic action, a temperature-responsive polymer compound having the UCST, i.e., showing a hydrophobic nature at low temperatures, is seemingly useful. At present, however, there are known temperature-responsive polymer compounds of few types having the UCST and it is difficult to newly develop temperature-responsive polymer compounds usable as efficient high-functional materials.

To obtain high-functional temperature-responsive polymer compounds, it is necessary to develop temperature-responsive polymer compounds having novel characteristics which are not achieved by the existing ones. In general, it is considered that a temperature-responsiveness is expressed owing to the balance between a hydrophilic moiety and a hydrophobic moiety. For example, a temperature-responsive polymer compound becomes insoluble in water with an increase in the carbon atom number in the side chain thereof. It is, therefore, difficult to synthesize a temperature-responsive polymer compound having a side chain with a large carbon atom number.

DISCLOSURE OF INVENTION

Under these circumstances, an object of the present invention is to provide a heat-responsive polymer material having a side chain with a large carbon atom number and showing various polarities which is synthesized by introducing acid amide bond(s) and ester bond(s) respectively into a side chain at one or more sites in the polymer chain, and a process for producing the same. Another object of the present invention is to apply the above-mentioned heat-responsive polymer to the separation and purification of proteins, chemicals or biological samples such as bioengineering products and cells having various polarities.

Another object of the present invention is to provide a polymer compound the temperature-responsiveness of which can be controlled by changing the functional groups or composition of the monomers constituting the polymer. Another object of the present invention is to provide a temperature-responsive polymer compound having an aromatic ring and being expected as exerting a high hydrophobicity or an electronic interaction which cannot be achieved by the existing temperature-responsive polymer compounds. A still further object of the present invention is to provide separation materials such as chromatographic packings containing these temperature-responsive polymer compounds.

A further object of the present invention is to provide a heat-responsive polymer which has a side chain with a large carbon number capable of imparting a hydrophobic nature thereto together with a functional group having hydrogen-bonding properties.

The present invention aims at providing a material which undergoes interaction with substances including biological components with the use of the hydrogen-bonding properties and hydrophobic nature thereof and can show the LCST or the UCST even in an aqueous solution containing a salt. The present invention further aims at providing novel materials (chromatographic packings, etc.) for the separation, adsorption or release of substances with the use of the above-described polymer.

To synthesize a heat-responsive polymer material having a side chain with a large carbon atom number, the present inventors have produced a material having a side chain with a large carbon atom number by introducing acid amide bond(s) and ester bond(s) respectively into one or more sites in the side chain. Then they have found that the thus obtained material shows a heat-responsiveness and various polarities. The present inventors have further found that this material is applicable to the separation of bioengineering products (proteins, peptides, etc.) having various polarities. The present invention has been completed based on these findings.

The present inventors have conducted intensive studies and consequently found that a temperature-responsive polymer compound the temperature-responsiveness of which can be controlled can be synthesized by appropriately specifying functional groups of the monomer to be polymerized. The present inventors have further found that a temperature-responsive polymer compound the temperature-responsiveness of which can be controlled can be synthesized by appropriately specifying the functional groups or composition of two types of monomers to be copolymerized. The present inventors have furthermore found that adsorption and separation materials containing these temperature-responsive polymer compounds are applicable to the separation of various substances. The present invention has been completed based on these findings.

To obtain heat-responsive polymers having hydrogen-bonding properties and highly hydrophobic nature, the present inventors have synthesized hydroxyalkylamide monomers with a large carbon atom number in their alkyl groups and polymerized the same to give polymer materials having both of hydrogen-bonding groups and hydrophobic groups. They have found that these polymer materials show temperature-responsiveness. The present inventors have further found that these temperature-responsive polymer compounds are usable in materials for separating, adsorbing and releasing substances and thus various substances can be separated by applying these materials. The present invention has also been completed based on these findings.

Further, the present inventors have conducted intensive studies and consequently found that a temperature-responsive polymer compound, the temperature-responsiveness of which can be controlled, can be synthesized by introducing a hydrogen-bonding functional group and a hydrophobic group into a monomer followed by polymerization, or by copolymerizing such a monomer with another polymerizable monomer. The present inventors have also found that adsorption/separation materials containing the above temperature-responsive polymer compound are applicable to the separation of various substances. The present invention has been completed based on these findings.

Accordingly, the present invention provides a polymer compound comprising polymer subunits as defined in groups A–E and with the total or relative number of individual monomer units as given.

Group A:

(1)

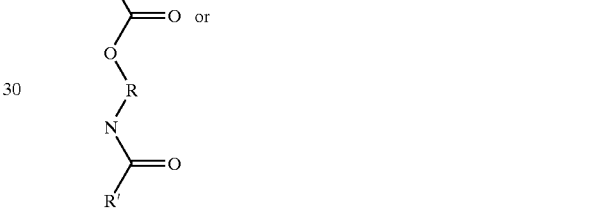

(2)

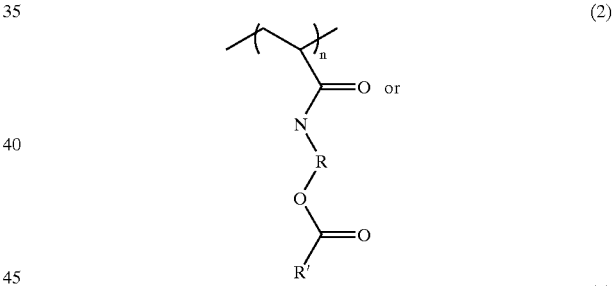

(3)

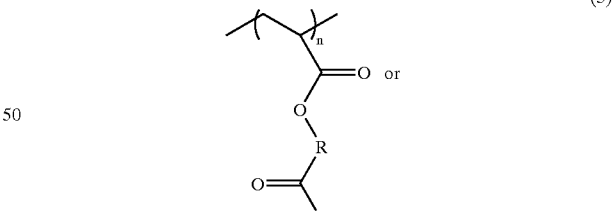

(4)

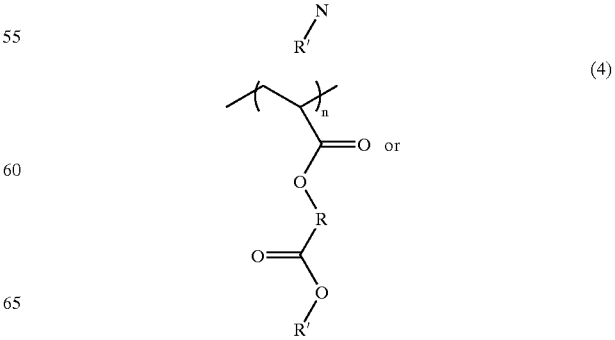

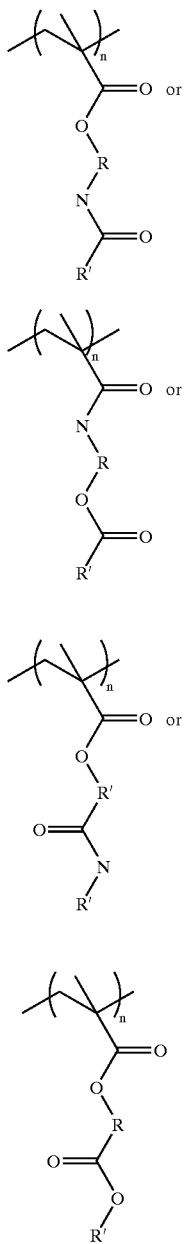

(5)
(6)
(7)
(8)

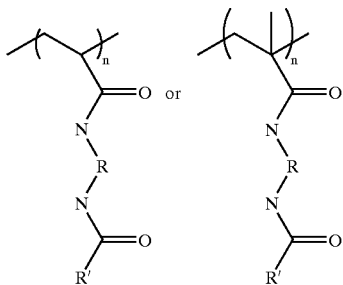

Group B:

wherein R represents a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms; R' represents a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and n is an integer of 2 or above.

Group C-1:

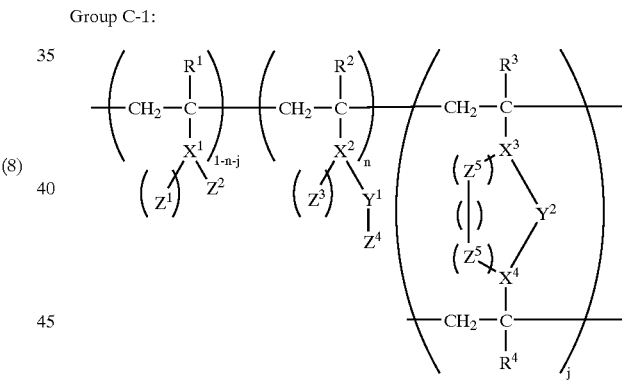

wherein n is the number of the middle kind of monomer unit, the number of the right kind of monomer unit, n is from 0.005 to 0.995 (inclusive) and j is from 0 to 0.5 (inclusive); $R^1$, $R^2$, $R^3$ and $R^4$ are the same or different and each represents a hydrogen atom or a methyl group; $X^1$, $X^2$, $X^3$ and $X^4$ are the same or different and each represents an acid amide group, an ester group or an ether group; $Y^1$ represents a linear or branched divalent aliphatic hydrocarbon group having 1 to 8 carbon atoms, a divalent alicyclic hydrocarbon group having 3 to 8 carbon atoms or a divalent aromatic hydrocarbon group having 6 to 14 carbon atoms; $Y^2$ represents a linear or branched divalent aliphatic hydrocarbon group having 1 to 8 carbon atoms, a divalent alicyclic hydrocarbon group having 3 to 8 carbon atoms, a linear or branched divalent aliphatic hydrocarbon group having 1 to 8 carbon atoms and one or more ether groups or a linear or branched divalent aliphatic hydrocarbon group having 1 to 8 carbon atoms and one or more hydroxyl groups; $Z^1$, $Z^2$, $Z^3$, wherein R represents a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms; R' represents a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and n is an integer of 2 or above.

$Z^5$ and $Z^6$ are the same or different and each represents a hydrogen atom, a linear or branched aliphatic hydrocarbon group having 1 to 8 carbon atoms, a linear or branched aliphatic hydrocarbon group having 1 to 8 carbon atoms and one or more hydroxyl groups, a linear or branched alicyclic hydrocarbon group having 1 to 8 carbon atoms and one or more hydroxyl group, a linear or branched aliphatic hydrocarbon group having 1 to 8 carbon atoms and one or more ether groups, a linear or branched alicyclic hydrocarbon group having 1 to 8 carbon atoms and one or more ether groups, a glycoside having 3 to 12 carbon atoms or a glycoside having 3 to 12 carbon atoms and carrying a linear or branched aliphatic hydrocarbon group having 1 to 8 carbon atoms, provided that $Z^1$, $Z^3$, $Z^5$ and $Z^6$ are functional groups bonded respectively to $X^1$, $X^2$, $X^3$ and $X^4$ when they are tertiary amide groups and $Z^5$ may be bonded to $Z^6$; and $Z^4$ represents a hydrogen atom, a hydroxyl group, an amide group, a nitryl group, a linear or branched aliphatic hydrocarbon group having 1 to 8 carbon atoms, a linear or branched aliphatic hydrocarbon group having 1 to 8 carbon atoms and one or more amide groups, a linear or branched aliphatic hydrocarbon group having 1 to 8 carbon atoms and one or more carbonyl groups, a linear or branched aliphatic hydrocarbon group having 1 to 8 carbon atoms and one or more nitryl groups, or a linear or branched aliphatic hydrocarbon group having 1 to 8 carbon atoms and one or more hydroxyl groups.

Group C-2:

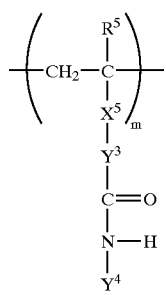

wherein $R^5$ represents a hydrogen atom or a methyl group; $X^5$ represents an acid amide group, an ester group or an ether group; $Y^3$ represents a linear or branched divalent aliphatic hydrocarbon group having 1 to 8 carbon atoms or a divalent alicyclic hydrocarbon group having 3 to 8 carbon atoms; and $Y^4$ represents a linear or branched aliphatic hydrocarbon group having 1 to 8 carbon atoms or a linear or branched aliphatic hydrocarbon group having 1 to 8 carbon atoms and one or more hydroxyl groups; n represent an integer 2 or more.

Group D:

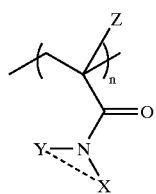

wherein Z represents a hydrogen atom or a methyl group; X represents a hydrogen atom or a linear or branched aliphatic hydrocarbon group having 1 to 8 carbon atoms and carrying at least one hydroxyl group; Y represents a linear or branched aliphatic hydrocarbon group having 2 to 8 carbon atoms and carrying at least one hydroxyl group, or X and Y may form together a chemical bond; and n is an integer of 2 or more.

Group E-1:

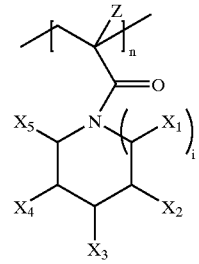

wherein Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); and i is an integer of from 0 to 6.

Group E-2:

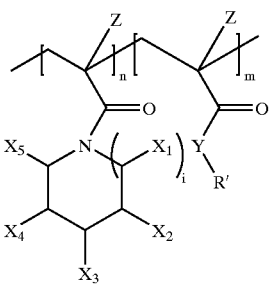

wherein n is the number of the left kind of monomer unit and m is the number of the right kind of monomer unit compared to the sum of them with n+m=1.0; Z represents a methyl group or a hydrogen atom; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); i is an integer of from 0 to 6; Y represents an oxygen atom or a nitrogen atom; and R' represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond or a hydrogen atom.

Group E-3:

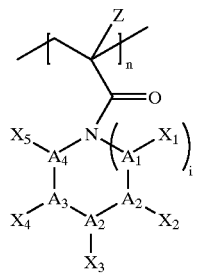

wherein Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); $A_1$, $A_2$, $A_3$, $A_4$ and $A_5$ are the same or different and each represents a carbon atom or a nitrogen atom bonding to $X_n$ (wherein n is an integer of 1 to 5) having a group —CO—NH—R or a group —CO—R, provided that at least one of $A_1$ to $A_5$ is a nitrogen atom bonding to $X_n$ (wherein n is an integer of 1 to 5) having a group —CO—NH—R or a group —CO—R (wherein R is as defined above); and i is an integer of from 0 to 6.

Group E-4:

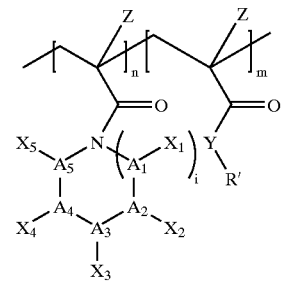

wherein n is the number of the left kind of monomer unit and m is the number of the right kind of monomer unit compared to the sum of them and with n+m=1.0; Z represents a methyl group or a hydrogen atom; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); $A_1$, $A_2$, $A_3$, $A_4$ and $A_5$ are the same or different and each represents a carbon atom or a nitrogen atom bonding to $X_n$ (wherein n is an integer of 1 to 5) having a group —CO—NH—R or a group —CO—R, provided that at least one of $A_1$ to $A_5$ is a nitrogen atom bonding to $X_n$ (wherein n is an integer of 1 to 5) having a group —CO—NH—R or a group —CO—R (wherein R is as defined above); i is an integer of from 0 to 6; Y represents an oxygen atom or a nitrogen atom; and R' represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond or a hydrogen atom.

Group E-5:

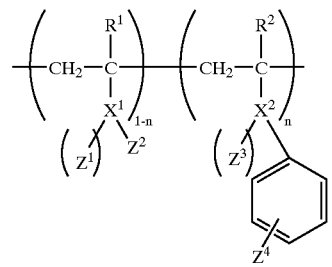

wherein n is the number of the right kind of monomer unit compared to the total number of the two kinds of monomer units shown and an arbitrary value falling within the range $0.005 \leq n \leq 0.9905$; $R^1$ and $R^2$ are the same or different and each represents a hydrogen atom or a methyl group; $X^1$ and $X^2$ are the same or different and each represents an acid amide or ester group; $Z^1$, $Z^2$ and $Z^3$ are the same or different and each represents a hydrogen atom, a linear or branched aliphatic hydrocarbon group having 1 to 8 carbon atoms, a linear or branched hydrocarbon group having 1 to 8 carbon atoms and containing at least one hydroxyl group, a linear or branched hydrocarbon group having 1 to 8 carbon atoms and containing at least one ether group, a glycoside having 3 to 12 carbon atoms or a glycoside having 3 to 12 carbon atoms and containing a linear or branched hydrocarbon group having 1 to 8 carbon atoms, provided that $Z^1$ or $Z^3$ is a functional group carried by $X^1$ or $X^2$ which is an acid amide; and $Z^4$ represents a hydrogen atom, a hydroxyl group, an amide group, a linear or branched hydrocarbon group having 1 to 8 carbon atoms and containing at least one amide group, a linear or branched hydrocarbon group having 1 to 8 carbon atoms and containing at least one carbonyl group or a linear or branched hydrocarbon group having 1 to 8 carbon atoms and containing at least one hydroxyl group which may be attached at an arbitrary position, i.e., o-, m- or p-position.

The present invention further provides a heat-responsive polymer material which contains a polymer compound represented by the formula of Group A and shows a cloud point due to a temperature change in an aqueous solution.

The present invention further provides a chromatographic packing with a stationary phase containing a heat-responsive polymer material which contains a polymer compound represented by the formula of Group A and shows a cloud point due to a temperature change in an aqueous solution. In addition, the present invention further provides a method for separating substances characterized by comprising the steps:
(i) adsorbing/binding a substance to a stationary phase present on the chromatographic packing as described above,
(ii) changing the hydrophilic/hydrophobic balance of the surface of the stationary phase by changing the temperature, preferably by external means and preferably in one or more steps,
(iii) passing a mobile phase, preferably having a constant composition and preferably being a liquid through the chromatographic packing;

steps (ii) and (iii) effecting release and separation of the substance from the packing.

The present invention furthermore provides a process for producing a polymer compound represented by the formula of Group A characterized by using one of the following methods:
(1) reacting an acrylic/methacryl amide or acrylic/methacryl ester monomer having a primary amino group in its amine or ester part, respectively, (for example, 2-aminoethyl methacrylate) with an acid anhydride or lactone and purifying the thus obtained product followed by polymerization in a solvent;
(2) reacting an acrylic/methacryl amide or acrylic/methacryl ester monomer having a hydroxyl group in its amine or ester part with an acid chloride and purifying the thus obtained product followed by polymerization in a solvent;
(3) reacting an alkylamino alcohol with an acid anhydride, then reacting the thus obtained product with acrylic acid chloride or methacrylic acid chloride and purifying the thus obtained product followed by polymerization in a solvent; or
(4) synthesizing a poly(acryl/methacryl amide or ester) having a primary amino group (for example, poly-2-aminoethyl methacrylate) or its hydrochloride in its amino or alcohol part, respectively, and reacting the thus synthesized product with an acid anhydride or lactone in a solvent containing triethylamine.

The present invention further provides a material for separating or adsorbing biological samples comprising a polymer compound represented by the formula of Group A and having acid amide bonds at two or more sites in the polymer side chain.

In addition, the present invention provides a method for separating substances characterized by comprising the steps:
(i) adsorbing/binding a substance, for instance from a biological sample, to a stationary phase present on a chromatographic packing,
(ii) changing the hydrophilic/hydrophobic balance of the stationary phase by changing the temperature of the stationary phase, preferably by external means and preferably in one or more steps,
(iii) passing a mobile phase through the packing, preferably of essentially constant composition and preferably in liquid form;

steps (i) and (ii) effecting release and separation of the substance from the stationary phase, and wherein said stationary phase comprises a polymer compound represented by the formula of Group A and having amide bonds in the side chain at two or more sites in the polymer chain.

The present invention further provides a heat-responsive polymer material which contains a polymer compound represented by the formula of Group B and shows a cloud point due to a temperature change in an aqueous solution.

The present invention further provides a chromatographic packing/stationary phase containing a heat-responsive polymer material which contains a polymer compound represented by the formula of Group B and shows a cloud point due to a temperature change in an aqueous solution.

In addition, the present invention provides a method for separating substances characterized by comprising
(i) binding/adsorbing a substance to a stationary phase on a chromatographic packing as described above,
(ii) changing the hydrophilic/hydrophobic balance of the surface of the stationary phase by changing the temperature, preferably by external means and preferably in one or more steps, and
(iii) passing single mobile phase through the packing, steps (ii) and (iii) effecting release and separation of the substance from the stationary phase. In this aspect of the invention the stationary phase comprises a polymer compound complying with a member of Group B above.

The present invention furthermore provides a process for producing a polymer compound represented by the formula of Group B characterized by using one of the following methods:
(1) reacting a compound selected from among aminoalkyl acylamide, aminoalkyl methacrylamide, aminoalkyl acrylamide hydrochloride and aminoalkyl methacrylamide hydrochloride with an acid anhydride or lactone, and purifying the thus obtained product followed by polymerization in a solvent; and
(2) reacting an alkyl diamine with an acid anhydride or an alkyll acid chloride, or reacting a compound having an amino group and an amide bond in its molecule with acryloyl chloride or methacryloyl chloride, and then purifying the thus obtained product followed by polymerization in a solvent.

The present invention further provides a material for separating or adsorbing biological samples comprising a polymer compound represented by the formula of Group B and having acid amide bonds at two or more sites in the polymer side chain.

In addition, the present invention provides a method as just defined above. In this aspect the stationary phase comprises a polymer compound represented by the formula of Group B and having acid amide bonds in the side chain at two or more sites in the polymer chain.

The present invention furthermore provides the above-mentioned polymer compound of Group C-1 or Group C-2 characterized by containing an aromatic hydrocarbon group and said repeating unit of the polymer containing two or more amide or ester groups which are either the same or different.

The present invention furthermore provides a polymer compound selected form the group consisting of the polymers represented by the formula of Group C-1 or Group C-2 and crosslinked matters containing these polymers characterized by expressing a temperature-responsiveness of changing its characteristics under a temperature change.

In addition, the present invention provides the above-mentioned temperature-responsive polymer compound of Group C-1 or Group C-2 characterized by being obtained by copolymerizing monomers which do not express any temperature-responsiveness each as a homopolymer.

Moreover, the present invention provides the above-mentioned temperature-responsive polymer compound of Group C-1 or Group C-2 characterized in that the temperature-responsiveness thereof can be controlled by changing the composition or functional groups of the monomers constituting said polymer compound, the molecular weight of said polymer compound or the concentration of said polymer compound in a solution.

The present invention furthermore provides an adsorption and separation material characterized by containing the temperature-responsive polymer compound represented by the formula of Group C-1 or Group C-2. This material can be used in the kind of separation methods described above in which the stationary phase contains a polymer compound from group C-1 or C-2, possibly replacing the Group A or Group B polymer compound.

The present invention provides a polymer compound containing a repeating unit represented by the formula of Group D or a copolymer or gel structure containing this unit structure and showing temperature-responsiveness in a solution, a process for producing the same, and a material for separating, adsorbing and releasing a substance with the use of the same. In addition this aspect of the invention provides a separation method in analogy with those described above but with the stationary phase comprising a polymer compound selected from group D, possibly together with group A,B,C, and E polymers.

The present invention furthermore provides materials for separating, adsorbing and releasing substances characterized by containing the above-mentioned temperature-responsive polymer compound represented by the formula of Group E-1, Group E-2, Group E-3, Group E-4 or Group E-5.

In addition, the present invention provides a method for separating substances characterized by providing a chromatographic packing to which at least one of the polymer compounds of the formula of Group E-1, Group E-2, Group E-3, Group E-4 or Group E-5 is attached and then;

(i) binding/adsorbing a substances to the stationary phase;
(ii) changing the hydrophobic-hydrophilic balance and/or the hydrogen-bonding properties of the stationary phase by changing the temperature of the phase, preferably by external means and preferably in one or more steps;
(iii) passing a mobile phase, preferably of constant composition and preferably in liquid form, through the packing;

steps (ii) and (iii) effecting release and separation of the substance from the packing/stationary phase.

The present invention further provides a process for producing the monomer represented by the formula of Group E-1 which comprises reacting acrylic acid chloride, methacrylic acid chloride, anhydrous acrylic acid or anhydrous methacrylic acid with a cyclic secondary amine compound having an amide group.

The present invention further provides a process for producing the monomer represented by the formula of Group E-3 which comprises reacting acrylic acid chloride, methacrylic acid chloride, anhydrous acrylic acid or anhydrous methacrylic acid with a secondary amine compound having at least one acyl bond.

Moreover, the present invention provides a process for producing polymer compounds which comprises adding the monomers represented by the formulae of Group E-1, Group E-2, Group E-3 and Group E-4 optionally together with a polymerization initiator to a polymerization solvent and then polymerizing the same under light-irradiation or at such a temperature as to induce the formation of a radical from the polymerization initiator.

BEST MODE FOR CARRYING OUT THE INVENTION

Figure 1:
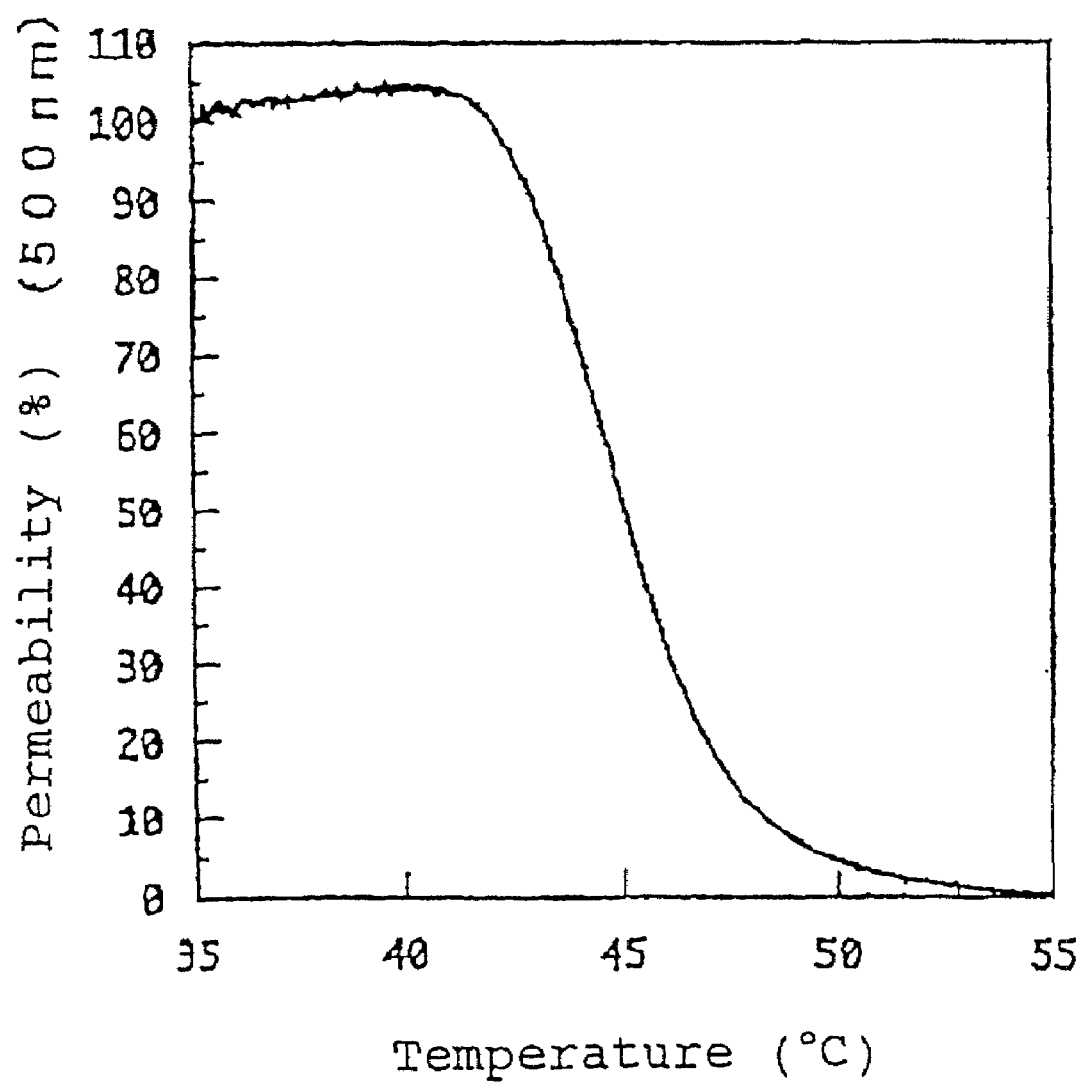
FIG. 1 provides a graph showing a relationship between the permeability and temperature of an aqueous solution of poly-methacryloyl-acetylaminoethyl-ester, obtained in Example A1.

The polymer compound according to the present invention has the following structure.

1. Compounds Represented by the Formula of Group A.

Group A:

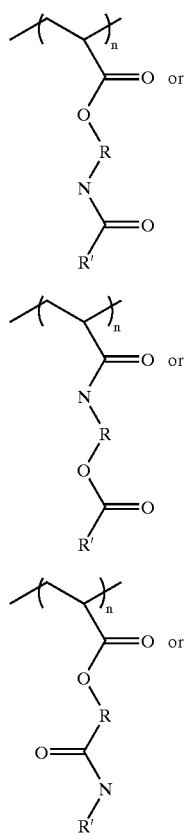

(1)

(2)

(3)

-continued

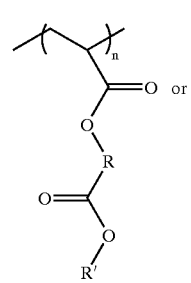

(4)

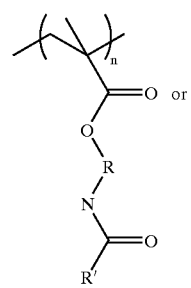

(5)

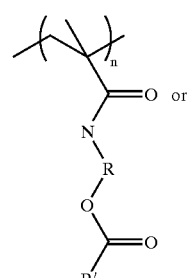

(6)

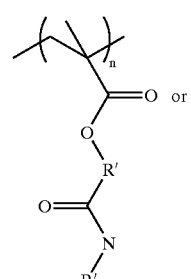

(7)

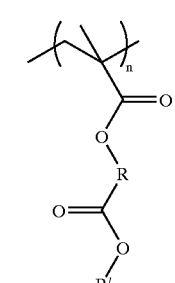

(8)

wherein R represents a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms; R' represents a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and n is an integer of 2 or above.

The term a "linear or branched aliphatic hydrocarbon group having 1 to 8 carbon atoms" as used in the formula of Group A of the present invention means a linear or branched alkyl group having 1 to 8 carbon atoms, a linear or branched alkenyl group having 2 to 8 carbon atoms or a linear or branched alkynyl group having 2 to 8 carbon atoms. The alkenyl group has one or more double bonds, while the alkynyl group has one or more triple bonds. Preferable examples of the alkyl group include methyl, ethyl, n-propyl, i-propyl, n-butyl, i-butyl, s-butyl and tbutyl groups. Preferable examples of the alkenyl group include vinyl, 1-propenyl, 2-propenyl (allyl), 1-butenyl, 2-butenyl and 3-butenyl groups. Preferable examples of the alkynyl groups include ethynyl, 1-propynyl, 2-propynyl (propargyl), 1-butynyl and 2-butynyl groups.

The term a "linear or branched divalent aliphatic hydrocarbon group having 1 to 8 carbon atoms" as used in the formula of Group A of the present invention means a linear or branched divalent alkyl group having 1 to 8 carbon atoms, a linear or branched divalent alkenyl group having 2 to 8 carbon atoms or a linear or branched divalent alkynyl group having 2 to 8 carbon atoms. The alkenyl group has one or more double bonds, while the alkynyl group has one or more triple bonds. Preferable examples of the linear or branched divalent alkyl group having 1 to 8 carbon atoms include methylene, ethylene, ethylidene, trimethylene, propylene (1,2-propanediyl), isopropylidene, tetramethylene, ethylethylene, pentamethylene and hexamethylene groups. Preferable examples of the linear or branched divalent alkenyl group having 2 to 8 carbon atoms include vinylene, vinylidene, propenylene, 1-butenylene, 2-butenylene, 1-pentenylene, 2-pentenylene, 1-hexenylene, 2-hexenylene and 3-hexenylene groups. Preferable examples of the linear or branched divalent alkynyl group having 2 to 8 carbon atoms include ethynylene, propynylene, 1-butynylene and 2-butynylene groups.

The term an "alicyclic hydrocarbon group having 3 to 8 carbon atoms" as used in the formula of Group A of the present invention means a cycloalkyl group having 3 to 8 carbon atoms or a cycloalkenyl group having 3 to 8 carbon atoms. The cycloalkenyl group has one or more double bonds. Preferable examples of the cycloalkyl group include cyclopropyl, cyclobutyl, cyclopentyl and cyclohexyl groups. Preferable examples of the cycloalkenyl group include 1-cyclopropen-1-yl, 2-cyclopropen-1-yl, 1-cyclobuten-1-yl, 2-cyclobuten-1-yl, 1-cyclopenten-1-yl, 2-cyclopenten-1-yl, 3-cyclopenten-1-yl, 1-cyclohexen-1-yl, 2-cyclohexn-1-yl and 3-cyclohexen-1-yl groups.

The term a "divalent alicyclic hydrocarbon group having 3 to 8 carbon atoms" as used in the formula of Group A of the present invention means a divalent cycloalkyl group having 3 to 8 carbon atoms or a divalent cycloalkenyl group having 3 to 8 carbon atoms. Preferable examples of the divalent cycloalkyl group having 3 to 8 carbon atoms include 1,2-cyclopropylene, 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, 1,2-cyclooctylene, 1,3-cyclooctylene, 1,4-cyclooctylene and 1,5-cyclooctylene groups. Preferable examples of the divalent cycloalkenyl group having 3 to 8 carbon atoms include 1-cyclopropen-1,2-enylene, 1-cyclobuten-1,2-enylene, 1-cyclobuten-3,4-ylene, 1-cyclohexen-1,2-enylene, 3-cyclohexen-1,2-ylene, 4-cyclohexen-1,2-ylene and 2,5-cyclohexadien-1,4-ylene.

The term an "aromatic hydrocarbon group having 6 to 14 carbon atoms" as used in the formula of Group A of the present invention means an aryl or aralkyl group having 6 to 14 carbon atoms. Preferable examples of the aromatic hydrocarbon group include phenyl, benzyl, phenethyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

The term a "divalent aromatic hydrocarbon group having 6 to 14 carbon atoms" as used in the formula of Group A of the present invention means a divalent aryl group or a divalent aralkyl group having 6 to 14 carbon atoms. Preferable examples of the divalent aromatic hydrocarbon group having 6 to 14 carbon atoms include o-phenylene, m-phenylene, p-phenylene, -o-φ-CH$_2$—, -m-φ-CH$_2$— and -p-φ-CH$_2$— groups wherein φ represents a benzene ring.

The term a "linear or branched aliphatic hydrocarbon group having one or more hydroxyl groups and 1 to 8 carbon atoms" as used in the formula of Group A of the present invention means an above-mentioned linear or branched aliphatic hydrocarbon group having 1 to 8 carbon atoms with substitution by one or more hydroxyl groups at arbitrary carbon atom(s). When it has two hydroxyl groups, these two hydroxyl groups may be attached to a carbon atom. Preferable examples thereof include hydroxymethyl, 2-hydroxyethyl, 1-hydroxyethyl, 1-hydroxy-n-propyl, 2-hydroxy-n-propyl, 3-hydroxy-n-propyl, 1-hydroxy-1-methylethyl, 2-hydroxy-1-methylethyl, 1-hydroxy-n-butyl, 2-hydroxy-n-butyl, 3-hydroxy-n-butyl, 4-hydroxy-n-butyl, 1-hydroxy-1-methyl-n-propyl, 2-hdyroxy-1-methyl-n-propyl, 3-hydroxy-2-methyl-n-propyl, 1-hydroxy-2-methyl-n-propyl, 2-hdyroxy-2-methyl-n-propyl, 3-hydroxy-2-methyl-n-propyl, 1-hydroxymethyl-1-methylethyl, 2-hydroxy-1,1-dimethylethyl, 1-hydroxyvinyl, 2-hydroxyvinyl, 1-hydroxyallyl, 2-hydroxyallyl, 3-hydroxyallyl, 2-hydroxy-1-methylvinyl and 1-hydroxymethylvinyl groups.

The term a "linear or branched aliphatic hydrocarbon group having one or more acid amide bonds and/or ester bonds and 2 to 9 carbon atoms" as used in the formula of Group A of the present invention means a linear or branched alkyl, alkenyl or alkynyl group with substitution by a group having one or more acid amide bonds and/or ester bonds at arbitrary carbon atom(s) which has 2 to 9 carbon atoms in total. Preferable examples thereof include acetyloxymethyl, 2-acetyloxy-ethyl, 3-acetyloxy-n-propyl, 1-acetyloxy-1,1-dimethyl-methyl, 4-acetyloxy-n-butyl, 2-acetyloxy-1,1-dimethyl-ethyl, 3-acetyloxy-1-methyl-n-propyl, 2-acetyloxy-2,2-dimethyl-ethyl, propionyloxymethyl, 2-propionyloxy-ethyl, 3-propionyloxy-n-propyl, 1-propionyloxy-1,1-dimethyl-methyl, acetamidomethyl, 2-acetamido-ethyl, 3-acetamido-n-propyl, 1-acetamido-1,1-dimethyl-ethyl, propionylaminomethyl, 2-propionylamino-ethyl, 3-propionylamino-n-propyl and 1-propionylamino-1,1-dimethylethyl groups.

The term a "linear or branched aliphatic hydrocarbon group having one or more acid amide bonds and/or ester bonds, one or more hydroxyl groups and 3 to 9 carbon atoms" as used in the formula of Group A of the present invention means a linear or branched alkyl, alkenyl or alkynyl group with substitution by a group having one or more acid amide bonds and/or ester bonds and one or more hydroxyl groups at arbitrary carbon atom(s) which has 3 to 9 carbon atoms in total. Preferable examples thereof include (1-hydroxypropionate)methyl, (1-hydroxypropionate)-ethyl, (1-hydroxypripionamino)methyl and (1-hydroxypropionamino)ethyl groups.

In the polymer compound represented by the above formula in the formula of Group A of the present invention, n is 2 or above. The value n may be controlled appropriately depending on the substance to be separated, etc. It is desirable that n is 5 or above.

The polymer compound represented by the formula of Group A according to the present invention can be obtained by one of the following methods.

(1) A monomer having a primary amino group (2-aminoethyl methacrylate, 2-aminoethyl methacrylate hydrochloride, etc.) is reacted with an acid anhydride (acetic anhydride, propionic anhydride, etc.) or lactone (propyl lactone, butyl lactone, etc.). The thus obtained product is purified by using a column and then polymerized in an appropriate solvent (methanol, ethanol, dimethyl sulfoxide, etc.). In this case, the substituent R in the polymer compound represented by the above formula can be controlled in size depending on the type of the monomer, while the substituent R' therein can be also controlled in size depending on the acid anhydride or lactone employed.

(2) A monomer having a hydroxyl group (2-hydroxethyl methacrylate, etc.) is reacted with an acid chloride (acetyl chloride, propionyl chloride, etc.). The thus obtained product was purified and then polymerized in an appropriate solvent (methanol, ethanol, dimethyl sulfoxide, etc.). In this case, the substituent R in the polymer compound represented by the above formula can be controlled in size depending on the type of the monomer, while the substituent R' therein can be also controlled in size depending on the acid chloride.

(3) An alkylamino alcohol (3-amino propanol, amino ethanol, etc.) is reacted with an acid anhydride (acetic anhydride, propionic anhydride, etc.). Then the thus obtained product is further reacted with acrylic acid chloride or methacrylic acid chloride. The resulting product is purified and then polymerized in an appropriate solvent (methanol, ethanol, dimethyl sulfoxide, etc.). In this case, the substituents R and R' in the polymer compound represented by the above formula can be controlled in size depending respectively on the alkylamino alcohol and the acid anhydride.

(4) Poly-2-aminoethyl methacrylate or its hydrochloride is synthesized and then reacted with an acid anhydride (acetic anhydride, propionic anhydride, etc.) or lactone (propyl lactone, butyl lactone, etc.) in a solvent containing triethylamine (TEA). In this case, the substituent R' can be controlled in size depending on the lactone or acid anhydride.

The term an "acid anhydride" means a carboxylic acid anhydride exemplified by acetic anhydride, propionic anhydride, butyric anhydride, isobutyric anhydride, valeric anhydride, isovaleric anhydride, capronic anhydride, maleic anhydride, etc.

The lactone is exemplified by β-propiolactone, γ-butyl lactone, γ-valerolactone, δ-valerolactone, γ-hexanolactone, δ-hexanolactone, ε-caprolactone, α-amino-γ-butyrolactone having an optically active group, etc.

The alkyl acid chloride is exemplified by acetyl chloride, propionyl chloride, butyrl chloride, valeroyl chloride, etc.

The reaction between the aminoalkyl (meth)acrylate (hydrochloride) [wherein the term "aminoalkyl (meth)acrylate hydrochloride" means one member selected from among aminoalkyl acrylate, aminoalkyl acrylate hydrochloride, aminoalkyl methacrylate and aminoalkyl methacrylate hydrochloride] and the acid anhydride is performed by adding a basic compound (for example, TEA) into a solvent (for example, an alcohol) and then slowly dropping one of the reactants thereinto. This reaction is carried out under ice-cooling and it is desirable to use methanol as the solvent.

After the completion of the reaction, the solvent is eliminated with an evaporator and the precipitate is taken up by filtration. Next, the target product is separated by column chromatography and purified by recrystallization.

The monomer thus purified is polymerized in an aqueous solution or organic solvent containing a polymerization initiator. After the completion of the polymerization reaction, reprecipitation is carried out in a solvent (for example, alcohol, acetone, ether, or a mixture thereof) to give the aimed polymer.

The cloud point of the obtained polymer can be arbitrarily controlled by varying the carbon atom number in the polymer side chain, the molecular weight, or the salt concentration. For example, the cloud point can be controlled by varying the concentration of the polymerization initiator or the monomer or by using a chain transfer agent such as 3-mercaptopropionic acid.

Alternatively, polymer materials having various cloud points can be synthesized by copolymerizing with other alkyl acrylamides or alkyl methacrylamides (N-isopropyl acrylamide, N-isopropyl methacrylamide, N-n-propyl acrylamide, N-n-propyl methacrylamide, etc.), or alkyl acrylates or alkyl methacrylates (butyl acrylate, butyl methacrylate, hydroxyethyl acrylate, hydroxyethyl methacrylate, glycidyl acrylate, glycidyl methacrylate, etc.).

It is also possible to synthesize a polymer the cloud point of which can be controlled depending on the pH environment by copolymerizing with an anionic monomer (acrylic acid, methacrylic acid, etc.) or a cationic monomer (acryloxyethyltriethylammonium, methacryloxyethyltriethylammonium, etc.).

It is considered that the phenomenon of the cloud point of the heat-responsive polymer is induced by the breakage or formation of the hydration water in the side chain or the intramolecular or intermolecular interaction among the polymer chains.

2. Compounds Represented by the Formula of Group B.

Group B:

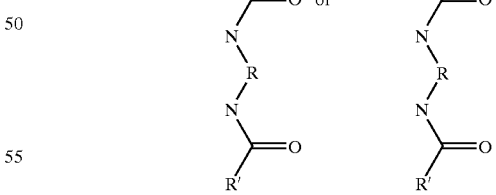

wherein R represents a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms; R' represents a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and n is an integer of 2 or above.

The term a "linear or branched aliphatic hydrocarbon group having 1 to 8 carbon atoms" as used in the formula of Group B of the present invention means a linear or branched alkyl group having 1 to 8 carbon atoms, a linear or branched alkenyl group having 2 to 8 carbon atoms or a linear or branched alkynyl group having 2 to 8 carbon atoms. The alkenyl group has one or more double bonds, while the alkynyl group has one or more triple bonds. Preferable examples of the alkyl group include methyl, ethyl, n-propyl, i-propyl, n-butyl, i-butyl, s-butyl and tbutyl groups. Preferable examples of the alkenyl group include vinyl, 1-propenyl, 2-propenyl (allyl), 1-butenyl, 2-butenyl and 3-butenyl groups. Preferable examples of the alkynyl groups include ethynyl, 1-propynyl, 2-propynyl (propargyl), 1-butynyl and 2-butynyl groups.

The term a "linear or branched divalent aliphatic hydrocarbon group having 1 to 8 carbon atoms" as used in the formula of Group B of the present invention means a linear or branched divalent alkyl group having 1 to 8 carbon atoms, a linear or branched divalent alkenyl group having 2 to 8 carbon atoms or a linear or branched divalent alkynyl group having 2 to 8 carbon atoms. The alkenyl group has one or more double bonds, while the alkynyl group has one or more triple bonds. Preferable examples of the linear or branched divalent alkyl group having 1 to 8 carbon atoms include methylene, ethylene, ethylidene, trimethylene, propylene (1,2-propanediyl), isopropylidene, tetramethylene, ethylethylene, pentamethylene, hexamethylene, heptamethylene and octamethylene groups. Preferable examples of the linear or branched divalent alkenyl group having 2 to 8 carbon atoms include vinylene, vinylidene, propenylene, 1-butenylene, 2-butenylene, 1-pentenylene, 2-pentenylene, 1-hexenylene, 2-hexenylene and 3-hexenylene groups. Preferable examples of the linear or branched divalent alkynyl group having 2 to 8 carbon atoms include ethynylene, propynylene, 1-butynylene and 2-butynylene groups.

The term an "alicyclic hydrocarbon group having 3 to 8 carbon atoms" as used in the formula of Group B of the present invention means a cycloalkyl group having 3 to 8 carbon atoms or a cycloalkenyl group having 3 to 8 carbon atoms. The cycloalkenyl group has one or more double bonds. Preferable examples of the cycloalkyl group include cyclopropyl, cyclobutyl, cyclopentyl and cyclohexyl groups. Preferable examples of the cycloalkenyl group include 1-cyclopropen-1-yl, 2-cyclopropen-1-yl, 1-cyclobuten-1-yl, 2-cyclobuten-1-yl, 1-cyclopenten-1-yl, 2-cyclopenten-1-yl, 3-cyclopenten-1-yl, 1-cyclohexen-1-yl, 2-cyclohexn-1-yl and 3-cyclohexen-1-yl groups.

The term a "divalent alicyclic hydrocarbon group having 3 to 8 carbon atoms" as used in the formula of Group B of the present invention means a divalent cycloalkyl group having 3 to 8 carbon atoms or a divalent cycloalkenyl group having 3 to 8 carbon atoms. Preferable examples of the divalent cycloalkyl group having 3 to 8 carbon atoms include 1,2-cyclopropylene, 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, 1,2-cyclooctylene, 1,3-cyclooctylene, 1,4-cyclooctylene and 1,5-cyclooctylene groups. Preferable examples of the divalent cycloalkenyl group having 3 to 8 carbon atoms include 1-cyclopropen-1,2-enylene, 1-cyclobuten-1,2-enylene, 1-cyclobuten-3,4-ylene, 1-cyclohexen-1,2-enylene, 3-cyclohexen-1,2-ylene, 4-cyclohexen-1,2-ylene and 2,5-cyclohexadien-1,4-ylene.

The term an "aromatic hydrocarbon group having 6 to 14 carbon atoms" as used in the formula of Group B of the present invention means an aryl or aralkyl group having 6 to 14 carbon atoms. Preferable examples of the aromatic hydrocarbon group include phenyl, benzyl, phenethyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

The term a "divalent aromatic hydrocarbon group having 6 to 14 carbon atoms" as used in the formula of Group B of the present invention means a divalent aryl group or a divalent aralkyl group having 6 to 14 carbon atoms. Preferable examples of the divalent aromatic hydrocarbon group having 6 to 14 carbon atoms include o-phenylene, m-phenylene, p-phenylene, -o-$\phi$-$CH_2$—, -m-$\phi$-$CH_2$— and -p-$\phi$-$CH_2$— groups wherein $\phi$ represents a benzene ring.

The term a "linear or branched aliphatic hydrocarbon group having one or more hydroxyl groups and 1 to 8 carbon atoms" as used in the formula of Group B of the present invention means an above-mentioned linear or branched aliphatic hydrocarbon group having 1 to 8 carbon atoms with substitution by one or more hydroxyl groups at arbitrary carbon atom(s). When it has two hydroxyl groups, these two hydroxyl groups may be attached to a carbon atom. Preferable examples thereof include hydroxymethyl, 2-hydroxyethyl, 1-hydroxyethyl, 1-hydroxy-n-propyl, 2-hydroxy-n-propyl, 3-hydroxy-n-propyl, 1-hydroxy-1-methylethyl, 2-hydroxy-1-methylethyl, 1-hydroxy-n-butyl, 2-hydroxy-n-butyl, 3-hydroxy-n-butyl, 4-hydroxy-n-butyl, 1-hydroxy-1-methyl-n-propyl, 2-hdyroxy-1-methyl-n-propyl, 3-hydroxy-1-methyl-n-propyl, 1-hydroxy-2-methyl-n-propyl, 2-hdyroxy-2-methyl-n-propyl, 3-hydroxy-2-methyl-n-propyl, 1-hydroxymethyl-1-methylethyl, 2-hydroxy-1,1-dimethylethyl, 1-hydroxyvinyl, 2-hydroxyvinyl, 1-hydroxyallyl, 2-hydroxyallyl, 3-hydroxyallyl, 2-hydroxy-1-methylvinyl and 1-hydroxymethylvinyl groups.

The term a "linear or branched aliphatic hydrocarbon group having one or more acid amide bonds and/or ester bonds and 2 to 9 carbon atoms" as used in the formula of Group B of the present invention means a linear or branched alkyl, alkenyl or alkynyl group with substitution by a group having one or more acid amide bonds and/or ester bonds at arbitrary carbon atom(s) which has 2 to 9 carbon atoms in total. Preferable examples thereof include acetyloxymethyl, 2-acetyloxy-ethyl, 3-acetyloxy-n-propyl, 1-acetyloxy-1,1-dimethyl-methyl, 4-acetyloxy-n-butyl, 2-acetyloxy-1,1-dimethyl-ethyl, 3-acetyloxy-1-methyl-n-propyl, 2-acetyloxy-2,2-dimethyl-ethyl, propionyloxymethyl, 2-propionyloxy-ethyl, 3-propionyloxy-n-propyl, 1-propionyloxy-1,1-dimethyl-methyl, acetamidomethyl, 2-acetamido-ethyl, 3-acetamido-n-propyl, 1-acetamido-1,1-dimethyl-ethyl, propionylaminomethyl, 2-propionylaminoethyl, 3-propionylamino-n-propyl and 1-propionylamino-1,1-dimethyl-methyl groups.

The term a "linear or branched aliphatic hydrocarbon group having one or more acid amide bonds and/or ester bonds, one or more hydroxyl groups and 3 to 9 carbon atoms" as used in the formula of Group B of the present invention means a linear or branched alkyl, alkenyl or alkynyl group with substitution by a group having one or more acid amide bonds and/or ester bonds and one or more hydroxyl groups at arbitrary carbon atom(s) which has 3 to 9 carbon atoms in total. Preferable examples thereof include (1-hydroxypropionate)methyl, (1-hydroxypropionate)ethyl, (1-hydroxypripionamino)methyl and (1-hydroxypropionamino)ethyl groups.

In the polymer compound represented by the formula of Group B in the present invention, n is 2 or above. The value n may be controlled appropriately depending on the substance to be separated, etc. It is desirable that n is 5 or above.

The polymer compound represented by the formula of Group B according to the present invention can be obtained by one of the following methods.

(1) A compound selected from among aminoalkyl acylamide, aminoalkyl methacrylamide, aminoalkyl acrylamide hydrochloride and aminoalkyl methacrylamide hydrochloride is reacted with an acid anhydride (acetic anhydride, propionic anhydride, etc.) or lactone (propyl lactone, butyl lactone, etc.). The thus obtained product is purified by using a column and then polymerized in an appropriate solvent (methanol, ethanol, dimethyl sulfoxide, etc.). In this case, the substituent R in the polymer compound represented by the above formula can be controlled in size depending on the size of the alkyl group carried by the monomer having an amino group, while the substituent R' therein can be also controlled in size depending on the acid anhydride or lactone employed.

(2) An alkyl diamine (ethylene diamine, trimethylene diamine, tetramethylene diamine, pentamethylene diamine, hexamethylene diamine, etc.) is reacted with an acid anhydride (acetic anhydride, propionic anhydride, etc.), an alkyl acid chloride (acetyl chloride, propionyl chloride, etc.) or di-t-butyl dicarbonate. Alternatively, a compound having an amino group and an amide bond in its molecule is reacted with acryloyl chloride or methacryloyl chloride. Then the thus obtained product is purified followed by polymerization in a solvent (methanol, ethanol, dimethyl sulfoxide, etc.). In this case, the substituent R in the polymer compound represented by the above formula can be controlled in size depending on the size of the alkylene in the alkyl diamine, while the substituent R' therein can be also controlled in size depending on the acid chloride.

The term an "acid anhydride" means a carboxylic acid anhydride exemplified by acetic anhydride, propionic anhydride, butyric anhydride, isobutyric anhydride, valeric anhydride, isovaleric anhydride, capronic anhydride, maleic anhydride, etc.

The lactone is exemplified by β-propiolactone, γ-butyl lactone, γ-valerolactone, δ-valerolactone, γ-hexanolactone, δ-hexanolactone, ε-caprolactone, α-amino-γ-butyrolactone having an optically active group, etc.

The reaction between the aminoalkyl acrylate, aminoalkyl acrylate hydrochloride, aminoalkyl methacrylate and aminoalkyl methacrylate hydrochloride and the acid anhydride is performed by adding a basic compound (for example, TEA) into a solvent (for example, an alcohol) and then slowly dropping one of the reactants thereinto. This reaction is carried out under ice-cooling and it is desirable to use methanol as the solvent.

After the completion of the reaction, the solvent is eliminated with an evaporator and the precipitate is taken up by filtration. Next, the target product is separated by column chromatography and purified by recrystallization.

The monomer thus purified is polymerized in an aqueous solution or organic solvent containing a polymerization initiator. After the completion of the polymerization reaction, reprecipitation is carried out in a solvent (for example, alcohol, acetone, ether, or a mixture thereof) to give the aimed polymer.

In the present invention, a similar compound can be obtained by reacting an alkyl diamines (1,3-propyldiamine, ethylene diamine, 1,6-hexamethylene diamine, 1,2-propane diamine, etc.) or a diamine (spermine, spermidine, etc.) with the equimolar amount of an acid anhydride or an alkyl acid chloride, further reacting the resultant product with acryloyl chloride or methacryloyl chloride and polymerizing the thus obtained monomer.

The cloud point of the obtained polymer can be arbitrarily controlled by varying the carbon atom number in the polymer side chain, the molecular weight, or the salt concentration. For example, the cloud point is liable to be lowered with an increase in the salt concentration of the aqueous solution.

Alternatively, polymer materials having various cloud points can be synthesized by copolymerizing with other alkyl acrylamides or alkyl methacrylamides (N-isopropyl acrylamide, N-isopropyl methacrylamide, N-n-propyl acrylamide, N-n-propyl methacrylamide, etc.), or alkyl acrylates or alkyl methacrylates (butyl acrylate, butyl methacrylate, hydroxyethyl acrylate, hydroxyethyl methacrylate, glycidyl acrylate, glycidyl methacrylate, etc.). A copolymer with n-butyl acrylamide shows a lowered cloud point, while one with acrylamide shows an elevated cloud point.

It is also possible to synthesize a polymer the cloud point of which can be controlled depending on the pH environment by copolymerizing with an anionic monomer (acrylic acid, methacrylic acid, etc.) or a cationic monomer (acryloxyethyltriethylammonium, methacryloxyethyltriethylammonium, etc.).

It is considered that the phenomenon of the cloud point of the heat-responsive polymer is induced by the breakage or formation of the hydration water in the side chain or the intramolecular or intermolecular interaction among the polymer chains.

3. Compounds Represented by the Formulae of Group C-1 and Group C-2.

Group C-1:

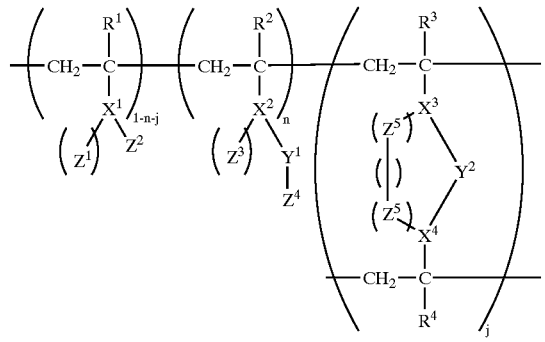

In the above formula of Group C-1, n is from 0.005 to 0.995 (inclusive), while j is from 0 to 0.5 (inclusive). $R^1$, $R^2$, $R^3$ and $R^4$ are the same or different and each represents a hydrogen atom or a methyl group. $X^1$, $X^2$, $X^3$ and $X^4$ are the same or different and each represents acid amides group, an ester group or an ether group. $Y^1$ represents a linear or branched divalent aliphatic hydrocarbon group having 1 to 8 carbon atoms, a divalent alicyclic hydrocarbon group having 3 to 8 carbon atoms or a divalent aromatic hydrocarbon group having 6 to 14 carbon atoms. $Y^2$ represents a linear or branched divalent aliphatic hydrocarbon group having 1 to 8 carbon atoms, a divalent alicyclic hydrocarbon group having 3 to 8 carbon atoms, a linear or branched divalent aliphatic hydrocarbon group having 1 to 8 carbon atoms and one or more ether groups or a linear or branched divalent aliphatic hydrocarbon group having 1 to 8 carbon atoms and one or more hydroxyl groups. $Z^1$, $Z^2$, $Z^3$, $Z^5$ and $Z^6$ are the same or different and each represents a hydrogen atom, a linear or branched aliphatic hydrocarbon group having 1 to 8 carbon atoms, a linear or branched aliphatic hydrocarbon group having 1 to 8 carbon atoms and one or more hydroxyl groups, a linear or branched alicyclic hydrocarbon group having 1 to 8 carbon atoms and one or more hydroxyl group, a linear or branched aliphatic hydrocarbon group having 1 to 8 carbon atoms and one or more ether groups, a linear or branched alicyclic hydrocarbon group having 1 to 8 carbon atoms and one or more ether groups, a glycoside having 3 to 12 carbon atoms or a glycoside having 3 to 12 carbon atoms and carrying a linear or branched aliphatic hydrocarbon group having 1 to 8 carbon atoms, provided that $Z^1$, $Z^3$, $Z^5$ and $Z^6$ are functional groups bonded respectively to $X^1$, $X^2$, $X^3$ and $X^4$ when they are tertiary amide groups and $Z^5$ may be bonded to $Z^6$. $Z^4$ represents a hydrogen atom, a hydroxyl group, an amide group, a nitryl group, a linear or branched aliphatic hydrocarbon group having 1 to 8 carbon atoms, a linear or branched aliphatic hydrocarbon group having 1 to 8 carbon atoms and one or more amide groups, a linear or branched aliphatic hydrocarbon group having 1 to 8 carbon atoms and one or more carbonyl groups, a linear or branched aliphatic hydrocarbon group having 1 to 8 carbon atoms and one or more nitryl groups, or a linear or branched aliphatic hydrocarbon group having 1 to 8 carbon atoms and one or more hydroxyl groups.

Group C-2:

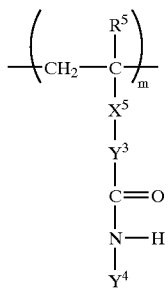

In the above formula, $R^5$ represents a hydrogen atom or a methyl group. $X^5$ represents an acid amide group, an ester group or an ether group. $Y^3$ represents a linear or branched divalent aliphatic hydrocarbon group having 1 to 8 carbon atoms or a divalent alicyclic hydrocarbon group having 3 to 8 carbon atoms. $Y^4$ represents a linear or branched aliphatic hydrocarbon group having 1 to 8 carbon atoms or a linear or branched aliphatic hydrocarbon group having 1 to 8 carbon atoms and one or more hydroxyl groups.

The term a "linear or branched aliphatic hydrocarbon group having 1 to 8 carbon atoms" as used in the formula of Group C-1 herein means a linear or branched alkyl group having 1 to 8 carbon atoms, a linear or branched alkenyl group having 1 to 8 carbon atoms or a linear or branched alkynyl group having 1 to 8 carbon atoms. The alkenyl group may have one or more double bonds while the alkynyl group may have one or more triple bonds. Preferable examples of the alkyl group include methyl, ethyl, n-propyl, isopropyl, n-butyl, isobutyl, s-butyl, t-butyl, n-pentyl, n-hexyl, n-heptyl and n-octyl groups. Preferable examples of the alkenyl group include vinyl, propenyl (1-propenyl), allyl, butenyl (wherein the double bond may be at an arbitrary site), pentenyl (wherein the double bond may be at an arbitrary site), hexenyl (wherein the double bond may be at an arbitrary site), heptenyl (wherein the double bond may be at an arbitrary site) and octenyl (wherein the double bond may be at an arbitrary site) groups. Preferable examples of the alkynyl group include ethynyl, propargyl, butynyl (wherein the triple bond may be at an arbitrary site), pentynyl (wherein the triple bond may be at an arbitrary site), hexynyl (wherein the triple bond may be at an arbitrary site), heptynyl (wherein the triple bond may be at an arbitrary site) and octynyl (wherein the triple bond may be at an arbitrary site) groups.

The term a "linear or branched divalent aliphatic hydrocarbon group having 1 to 8 carbon atoms" as used in the formulae of Group C-1 and Group C-2 herein means a linear or branched alkylene group having 1 to 8 carbon atoms, a linear or branched alkenylene group having 1 to 8 carbon atoms or a linear or branched alkynylene group having 1 to 8 carbon atoms. The alkenylene group may have one or more double bonds while the alkynylene group may have one or more triple bonds. Preferable examples of the alkylene group include methylene, ethylene, propylene, butylene, pentylene, hexylene, heptylene and octylene groups. Preferable examples of the alkenylene group include vinylene, propenylene (wherein the double bond may be at an arbitrary site), butenylene (wherein the double bond may be at an arbitrary site), pentenylene (wherein the double bond may be at an arbitrary site), hexenylene (wherein the double bond may be at an arbitrary site), heptenylene (wherein the double bond may be at an arbitrary site) and octenylene (wherein the double bond may be at an arbitrary site) groups. Preferable examples of the alkynylene group include ethynylene, propynylene (wherein the triple bond may be at an arbitrary site), butynylene (wherein the triple bond may be at an arbitrary site), pentynylene (wherein the triple bond may be at an arbitrary site), hexynylene (wherein the triple bond may be at an arbitrary site), heptynylene (wherein the triple bond may be at an arbitrary site) and octynylene (wherein the triple bond may be at an arbitrary site) groups.

The term a "divalent alicyclic hydrocarbon group having 3 to 8 carbon atoms" as used in the formulae of Group C-1 and Group C-2 herein means a cycloalkylene group having 3 to 8 carbon atoms or a cycloalkenylene group having 3 to 8 carbon atoms. The cycloalkenylene group may have one or more double bonds. Preferable examples of the cycloalkylene group include cyclopropylene, cyclobutylene, cyclopentylene, cyclohexylene, cycloheptylene and cyclooctylene groups. Preferable examples of the cycloalkenylene group include cyclopropenylene (wherein the double bond may be at an arbitrary site), cyclobutenylene (wherein the double bond may be at an arbitrary site), cyclopentenylene (wherein the double bond may be at an arbitrary site), cyclohexenylene (wherein the double bond may be at an arbitrary site), cycloheptenylene (wherein the double bond may be at an arbitrary site) and cyclooctenylene (wherein the double bond may be at an arbitrary site) groups.

The term a "divalent aromatic hydrocarbon group having 6 to 14 carbon atoms" as used in the formulae of Group C-1 and group C-2 herein means an arylene or aralkylene group having 6 to 14 carbon atoms. Preferable examples of the aromatic hydrocarbon group include phenylene, benzylene, phenethylene, naphthylene, anthrylene and phenanthrylene groups.

The term a "linear or branched aliphatic hydrocarbon group having 1 to 8 carbon atoms and one or more hydroxyl groups" as used in the formulae of Group C-1 and Group C-2 herein means the linear or branched aliphatic hydrocarbon group having 1 to 8 carbon atoms as described above wherein one or more carbon atoms at arbitrary sites carry hydroxyl groups. When it has two hydroxyl groups, these hydroxyl groups may be attached to a single carbon atom.

The term a "linear or branched divalent aliphatic hydrocarbon group having 1 to 8 carbon atoms and one or more hydroxyl groups" as used in the formulae of Group C-1 and Group C-2 herein means the linear or branched divalent aliphatic hydrocarbon group having 1 to 8 carbon atoms as described above wherein one or more carbon atoms at arbitrary sites carry hydroxyl groups. When it has two hydroxyl groups, these hydroxyl groups may be attached to a single carbon atom.

The term a "linear or branched alicyclic hydrocarbon group having 1 to 8 carbon atoms and one or more hydroxyl groups" as used in the formulae of Group C-1 and group C-2 herein means the linear or branched alicyclic hydrocarbon group having 1 to 8 carbon atoms as described above wherein one or more carbon atoms at arbitrary sites carry hydroxyl groups. When it has two or more hydroxyl groups, these hydroxyl groups may be attached to a single carbon atom.

The term a "linear or branched aliphatic hydrocarbon group having 1 to 8 carbon atoms and one or more ether groups" as used in the formulae of Group C-1 and Group C-2 herein means the linear or branched aliphatic hydrocarbon group having 1 to 8 carbon atoms as described above wherein one or more ether groups are introduced into arbitrary sites.

The term a "linear or branched divalent aliphatic hydrocarbon group having 1 to 8 carbon atoms and one or more ether groups" as used in the formulae of Group C-1 and Group C-2 herein means the linear or branched divalent aliphatic hydrocarbon group having 1 to 8 carbon atoms as described above wherein one or more ether groups are introduced into arbitrary sites.

The term a "linear or branched alicyclic hydrocarbon group having 1 to 8 carbon atoms and one or more ether groups" as used in the formulae of Group C-1 and Group C-2 herein means the linear or branched alicyclic hydrocarbon group having 1 to 8 carbon atoms as described above wherein one or more ether groups are introduced into arbitrary sites.

The term a "glycoside having 3 to 12 carbon atoms" as used in the formulae of Group C-1 and Group C-2 herein means an aldose or a ketose formed by a glycoside bond and having 3 to 12 carbon atoms. Preferable examples of the aldose or ketose include arabinose, lyxose, ribose, xylose, glucose, galactose, mannose and fructose.

The term a "linear or branched aliphatic hydrocarbon group having 1 to 8 carbon atoms and a glycoside having 3 to 12 carbon atoms" as used in the formulae of Group C-1 and Group C-2 herein means the above-mentioned linear or branched aliphatic hydrocarbon group having 1 to 8 carbon atoms wherein the above-mentioned glycoside having 3 to 12 carbon atoms is bonded via a glycoside bond to the arbitrary site.

The term a "linear or branched aliphatic hydrocarbon group having 1 to 8 carbon atoms and one or more amide groups" as used in the formulae of Group C-1 and Group C-2 herein means the linear or branched aliphatic hydrocarbon group having 1 to 8 carbon atoms as described above wherein one or more amide groups are introduced into arbitrary sites.

The term a "linear or branched aliphatic hydrocarbon group having 1 to 8 carbon atoms and one or more carbonyl groups" as used in the formulae of Group C-1 and Group C-2 herein means the linear or branched aliphatic hydrocarbon group having 1 to 8 carbon atoms as described above wherein one or more carbonyl groups are introduced into arbitrary sites.

The term a "linear or branched aliphatic hydrocarbon group having 1 to 8 carbon atoms and one or more nitryl groups" as used in the formulae of Group C-1 and Group C-2 herein means the linear or branched aliphatic hydrocarbon group having 1 to 8 carbon atoms as described above wherein one or more nitryl groups are introduced into arbitrary sites. When it has two nitryl groups, these nitryl groups may be attached to a single carbon atom.

The polymer compound represented by the formula of Group C-1 and Group C-2 according to the present invention can be produced in the following manner. First, one or more monomers serving as the starting material(s) of the polymer compound and a polymerization initiator are dissolved in a solvent and the polymerization reaction is initiated by, for example, heating. In this step, a bifunctional monomer (a crosslinking agent) may be also dissolved in the solvent to give a crosslinked polymer. It is also possible in this step to dissolve a chain transfer agent in the polymerization solvent so as to control the molecular weight of the polymer compound or to introduce a reactive functional group to the terminal of the polymer compound. After the completion of the polymer reaction, the polymer compound is not dissolved but re-precipitated from the solvent thereby giving the aimed temperature-responsive polymer compound.

The polymer compound represented by the formula of Group C-1 and Group C-2 according to the present invention can be fixed onto the surface of a support (silica gel, polymer gel, etc.) with the use of, for example, the reactive functional group having been introduced into the terminal thereof. Alternatively, a polymerization initiator, etc. is fixed onto the surface of a solid (silica gel, polymer gel, etc.) and then one or more monomers serving as the starting material(s) of the polymer compound are dissolved in a polymerization solvent. Next, the polymerization reaction is started by, for example, heating in the presence of the support (silica gel, polymer gel, etc.) carrying the polymerization initiator thereon to thereby fix the polymer compound onto the surface of the support (silica gel, polymer gel, etc.). In this case, a bifunctional monomer (a crosslinking agent) may be dissolved in the solvent to give a crosslinked matter containing the polymer compound. It is also possible in this step to dissolve a chain transfer agent in the polymerization solvent so as to control the molecular weight of the polymer compound or to introduce a reactive functional group to the terminal of the polymer compound. Materials containing the thus obtained polymer compounds are applicable to adsorption and separation materials such as various liquid chromatographic packings, drug carriers, dielectric and magnetic materials, piezoelectric and pyroelectric materials, degradable and reactive materials, biofunctional materials, etc.

4. Compounds Represented by the Formula of Group D.

The polymer compound according to the present invention has the following structure. Namely, a polymer material comprising a polymer compound consisting exclusively of a repeating unit represented by the following formula (I) or a copolymer or a gel containing this unit structure and showing temperature-responsiveness in a solution.

Group D:

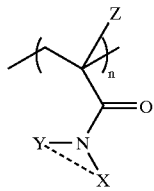

wherein Z represents a hydrogen atom or a methyl group: X represents a hydrogen atom or a linear or branched aliphatic hydrocarbon group having 1 to 8 carbon atoms and carrying at least one hydroxyl group; Y represents a linear or branched aliphatic hydrocarbon group having 2 to 8 carbon atoms and carrying at least one hydroxyl group, or X and Y may form together a chemical bond; and n is an integer of 2 or more.

The term "linear or branched aliphatic hydrocarbon group having 1 to 8 carbon atoms and carrying at least one hydroxyl group" as used in the formula of Group D in the present invention means a linear or branched hydroxyl alkyl group having 1 to 8 carbon atoms, while the term "linear or branched aliphatic hydrocarbon group having 2 to 8 carbon atoms and carrying at least one hydroxyl group" as used herein means a linear or branched hydroxyalkyl group having 2 to 8 carbon atoms.

The term "X and Y form together a chemical bond" as used in the formula of Group D in the present invention means that X and Y have each an aliphatic hydrocarbon group and form together a chemical bond structure having 5 to 16 carbon atoms in total (i.e., X+Y) and at least one hydroxyl group. The term "X and Y form together a chemical bond" means that X and Y are covalently bonded to each other.

The hydroxyalkyl group has one or more hydroxyl groups. Preferable examples of the hydroxyalkyl group include 1-hydroxypentyl, 2-hydroxypentyl, 3-hydroxypentyl, trans-hydroxycyclohexyl, 6-hydroxyhexyl, 2-hydroxy-3-methylpentyl, 5-hydroxy-3-ethylpentyl, 3-hydroxyhexyl, 7-hydroxyheptyl, 6-hydroxyheptyl, 8,3-dihydroxyoctyl and 8,5-dihydroxyoctyl groups.

Although n is not particularly restricted so long as it is an integer of 2 or more, it preferably stands for a value giving a molecular weight of not more than 700,000, still preferably from 1,000 to 700,000.

The monomer represented by the formula of Group D is exemplified by compounds which are synthesized by reacting acrylic acid chloride, methacrylic acid chloride, anhydrous acrylic acid or anhydrous methacrylic acid with alkylamino alcohols. The "alkylamino alcohols" usable in the present invention are those having a linear or branched aliphatic hydrocarbon group having 3 to 16 carbon atoms and at least one hydroxyl group or those having an alicyclic hydrocarbon group having a cyclic structure with 3 to 16 carbon atoms and at least one hydroxyl group. Preferable examples of the alkylamino alcohols include those having 1 to 12 carbon atoms and at least one hydroxyl group such as 4-aminopentanol, 5-aminopentanol, 3-aminopentanol, 2-aminopentanol, trans-aminopentanol, 6-aminohexanol and N-5-hydroxypentyl-N'-methyl-8-amino-3,5-dihydroxyoctyl.

The copolymer containing the above-mentioned repeating unit to be used in the present invention means a random copolymer or a block copolymer of the monomer represented by the above chemical formula with other monomers, for example, alkylacrylamides (t-butylacrylamide, n-butylacrylamide, i-butylacrylamide, acrylamide, hexylacrylamide, heptylacrylamide, etc.), alkylmethacrylamides (t-butylmethacrylamide, n-butylmethacrylamide, butylmethacrylamide, hexylmethacrylamide, heptylmethacrylamide, etc.), methacrylic acid, alkyl acrylates (n-butyl acrylate, s-butyl acrylate, t-butyl acrylate, n-propyl acrylate, i-propyl acrylate, etc.), alkyl methacrylates (methyl methacrylate, n-butyl methacrylate, s-butyl methacrylate, t-butyl methacrylate, n-propyl methacrylate, i-propyl methacrylate, etc.), monomers having functional groups such as hydroxyl, amino, sulfone and epoxy groups (hydroxyethyl methacrylate, hydroxyethylarcylamide, 2-aminoethylmethacrylamide, aminostyrene, 2-(t-butylamino)-ethyl methacrylate, 2-sulfoethyl methacrylate, 3-sulfopropyl acrylate, glycidyl methacrylate, etc.) and styrene.

The term "gel structure" as used herein means one obtained by reacting the polymer with a crosslinking agent such as methylene bisacrylamide.

The polymer compound represented by the formula of Group D according to the present invention is produced in the following manner. One or more monomers serving as the starting materials of the polymer compound and a polymerization initiator are dissolved in a polymerization solvent. Then the polymerization is initiated by, for example, heating. In this step, a bifunctional monomer may be dissolved to give a gel structure containing the desired polymer compound. It is also possible in this step to dissolve a chain transfer agent in the polymerization solvent too so as to control the molecular weight of the polymer compound, or to introduce a reactive functional group into the terminal of the polymer compound. After the completion of the polymerization reaction, re-precipitation is carried out in a solvent in which the desired polymer is insoluble. Thus, the stimulus-responsive polymer compound can be obtained at the desired temperature.

The polymer compound represented by the formula of Group D according to the present invention can be fixed onto the surface of a carrier (silica gel, polymer gel, etc.) with the use of, for example, a reactive functional group having been introduced into the terminal thereof. Alternatively, the polymer compound can be fixed on the surface of a carrier (silica gel, polymer gel, etc.) by fixing a polymerization initiator on the surface of a solid (silica gel, polymer, etc.), dissolving one or more monomers serving as the starting materials of the polymer compound in a polymerization solvent, and then effecting a polymerization reaction, for example, under heating in the presence of the carrier (silica gel, polymer gel, etc.) having the polymerization initiator fixed thereon. Similar to the above-described case, a bifunctional monomer may be dissolved in this step to give a gel structure containing the desired polymer compound. It is also possible in this step to dissolve a chain transfer agent in the polymerization solvent too so as to control the molecular weight of the polymer compound or to introduce a reactive functional group thereinto. Materials containing such a polymer compound are applicable to various adsorption/separation carriers (liquid chromatographic packings, adsorbents, etc.), agents for releasing bioengineering products, etc. and biofunctional materials.

5. Compounds Represented by the Formulae of Group E-1, Group E-2, Group E-3, Group E-4 and Group E-5.

Group E-1:

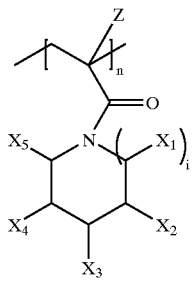

wherein Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); and i is an integer of from 0 to 6.

Group E-2:

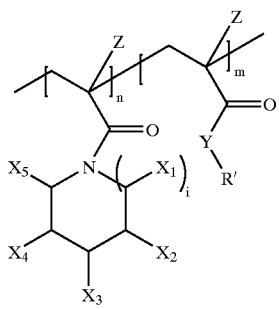

wherein n and m are each such an arbitrary value as to make n+m= 1.0; Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); i is an integer of from 0 to 6; Y represents an oxygen atom or a nitrogen atom; and R' represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond or a hydrogen atom.

Group E-3:

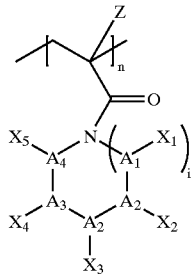

wherein Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); $A_1$, $A_2$, $A_3$, $A_4$ and $A_5$ are the same or different and each represents a carbon atom or a nitrogen atom bonding to $X_n$ (wherein n is an integer of 1 to 5) having a group —CO—NH—R or a group —CO—R, provided that at least one of $A_1$ to $A_5$ is a nitrogen atom bonding to $X_n$ (wherein n is an integer of 1 to 5) having a group —CO—NH—R or a group —CO—R (wherein R is as defined above); and i is an integer of from 0 to 6.

Group E-4:

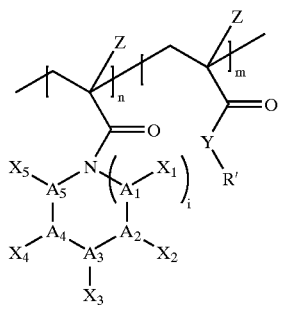

wherein n and m are each such an arbitrary value as to make n+m= 1.0; Z represents a methyl group or a hydrogen atom; n is an integer of 2 or more; $X_1$, $X_2$, $X_3$, $X_4$ and $X_5$ are the same or different and each represents a hydrogen atom, a group R, or a group —CO—NH—R, provided that at least one of $X_1$ to $X_5$ is a group —CO—NH—R (wherein R represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond, or a hydrogen atom); $A_1, A_2, A_3, A_4$ and $A_5$ are the same or different and each represents a carbon atom or a nitrogen atom bonding to $X_n$ (wherein n is an integer of 1 to 5) having a group —CO—NH—R or a group —CO—R, provided that at least one of $A_1$ to $A_5$ is a nitrogen atom bonding to $X_n$ (wherein n is an integer of 1 to 5) having a group —CO—NH—R or a group —CO—R (wherein R is as defined above); i is an integer of from 0 to 6; Y represents an oxygen atom or a nitrogen atom; and R' represents a linear or branched aliphatic hydrocarbon group having 1 to 6 carbon atoms, a linear or branched aliphatic hydrocarbon group having 1 to 10 carbon atoms and containing at least one amide bond, a linear or branched aliphatic hydrocarbon group having 1 to 10 carbon atoms and containing at least one hydroxyl group, an alicyclic hydrocarbon group having 3 to 10 carbon atoms and containing at least one hydroxyl group, an alicyclic hydrocarbon group having 3 to 10 carbon atoms and containing at least one amide bond or a hydrogen atom.

Group E-5:

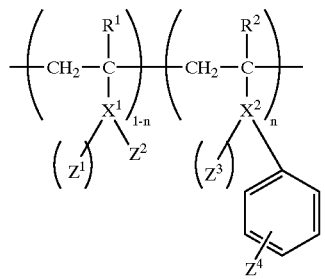

wherein n is n is the number of the right kind of monomer unit compared to the total number of the two kinds of monomer units shown and is an arbitrary value falling within the range $0.005 \leq n \leq 0.995$; $R^1$ and $R^2$ are the same or different and each represents a hydrogen atom or a methyl group; $X^1$ and $X^2$ are the same or different and each represents an acid amide or ester group; $Z^1$, $Z^2$ and $Z^3$ are the same or different and each represents a hydrogen atom, a linear or branched aliphatic hydrocarbon group having 1 to 8 carbon atoms, a linear or branched hydrocarbon group having 1 to 8 carbon atoms and containing at least one hydroxyl group, a linear or branched hydrocarbon group having 1 to 8 carbon atoms and containing at least one ether group, a glycoside having 3 to 12 carbon atoms or a glycoside having 3 to 12 carbon atoms and containing a linear or branched hydrocarbon group having 1 to 8 carbon atoms, provided that $Z^1$ or $Z^3$ is a functional group carried by $X^1$ or $X^2$ which is a tertiary amide; and $Z^4$ represents a hydrogen atom, a hydroxyl group, an amide group, a linear or branched hydrocarbon group having 1 to 8 carbon atoms and containing at least one amide group, a linear or branched hydrocarbon group having 1 to 8 carbon atoms and containing at least one carbonyl group or a linear or branched hydrocarbon group having 1 to 8 carbon atoms and containing at least one hydroxyl group which may be attached at an arbitrary position, i.e., o-, m- or p-position.

The term "linear or branched aliphatic hydrocarbon group having 1 to 6 carbon atoms" as used in the formulae of Group E-1, Group E-2, Group E-3, Group E-4 and Group E-5 in the present invention means a linear or branched alkyl group having 1 to 6 carbon atoms, a linear or branched alkenyl group having 1 to 6 carbon atoms or a linear or branched alkynyl group having 1 to 6 carbon atoms. Among all, alkyl groups are preferable therefor. Still preferable examples thereof include methyl, ethyl, n-propyl, i-propyl, n-butyl, i-butyl, s-butyl, t-butyl, n-pentyl and n-hexyl groups.

The term "aliphatic hydrocarbon group having 1 to 10 carbon atoms and containing at least one amide bond" as used in the formulae of Group E-1, Group E-2, Group E-3, Group E-4 and Group E-5 herein means a linear or branched aliphatic hydrocarbon group having 1 to 10 carbon atoms and containing one or more amide bonds at arbitrary positions.

The term "aliphatic hydrocarbon group having 1 to 6 carbon atoms and containing at least one hydroxyl group" as used in the formulae of Group E-1, Group E-2, Group E-3, Group E-4 and Group E-5 herein means a linear or branched aliphatic hydrocarbon group having 1 to 10 carbon atoms and containing one or more hydroxyl groups at arbitrary positions. Preferable examples thereof include hydroxymethyl, 2-hydroxyethyl, 3-hydroxypropyl, 5-hydroxyisopropyl, 4-hydroxybutyl, 5-hydroxypentyl, 6-hydroxyhexyl, 5,7-dihydroxybutyl, 6,8-dihydroxyoctyl, 5,9-dihydroxynonyl and 5,7,10-trihydroxydecyl groups.

The term "alicyclic hydrocarbon group having 3 to 10 carbon atoms and containing at least one hydroxyl group" as used in the formulae of Group E-1, Group E-2, Group E-3, Group E-4 and Group E-5 herein means a hydroxycycloalkyl group having 3 to 10 carbon atoms. Preferable examples thereof include 4-hydoxycyclohexyl, 1-methyl-4-hydroxycyclohexyl, 2-hdyroxy-cyclopropyl and 3,5-dihdyroxycyclooctyl groups.

The term "alicyclic hydrocarbon group having 3 to 10 carbon atoms and containing at least one amide bond" as used in the formulae of Group E-1, Group E-2, Group E-3, Group E-4 and Group E-5 herein means an alicyclic group having 3 to 10 carbon atoms and containing one or more amide groups at arbitrary positions.

The "cyclic secondary amine compound having an amide group" usable in the formulae of Group E-1, Group E-2, Group E-3, Group E-4 and Group E-5 herein for synthesizing the monomer represented by the formula of Group E-1 means a cyclic secondary amine compound having 5 to 30 carbon atoms and containing one or more amide bonds or a cyclic secondary amine compound having 5 to 30 carbon atoms and containing one or more hydroxyl groups and amide bonds. Preferable examples thereof include 4-piperidine-carboxamide, N-methyl-4-piperidinecarboxamide, N-4-hydroxybutyl-4-piperidine-caroxamide, N-butyl-4-piperidine-carboxamide, 2-piperidinecarboxamide, N-methyl-2-piperidine-carboxamide and N,N'-dimethyl-2,4-piperidine-carboxamide.

The "cyclic secondary amine compound having at least one acyl bond" usable herein for synthesizing the monomer represented by the formula of Group E-3 means a cyclic secondary amine compound having 5 to 30 carbon atoms and containing one or more amide bonds or a cyclic secondary amine compound having 5 to 30 carbon atoms and containing one or more acyl bond. Preferable examples thereof include 1-acetylpiperazine, 1-propionylpiperazine, 1-isobutyrylpiperazine, 1-hydroxybutyl-piperazine, 1-valerylpiperazine and 1-hydroxyvaleryl-piperazine.

The polymer compound represented by each of the formulae of Group E-1, Group E-2, Group E-3, Group E-4 and Group E-5 according to the present invention is produced in the following manner. One or more monomers serving as the starting materials of the polymer compound and a polymerization initiator are dissolved in a polymerization solvent. Then the polymerization is initiated by, for example, heating. In this step, a bifunctional monomer (i.e., a crosslinking agent) may be dissolved to give a crosslinked matter containing the desired polymer compound. It is also possible to dissolve a chain transfer agent in the polymerization solvent too so as to control the molecular weight of the polymer compound or to introduce a reactive functional group into the terminal of the polymer compound. After the completion of the polymerization reaction, re-precipitation is carried out in a solvent in which the desired polymer is insoluble. Thus, the desired temperature-responsive polymer compound can be obtained.

Functional groups (for example, carboxyl, hydroxyl, amino, nitryl, linear or branched alkyl having 1 to 20 carbon atoms and cyano groups) may be introduced into the polymer chain terminal of the polymer compound represented by the formula of Group E-1, Group E-2, Group E-3, Group E-4 or Group E-5 according to the present invention. The introduction can be carried out by conventionally known methods. If necessary, it is possible in this step to use a chain transfer agent or a polymerization initiator. For example, use can be made therefor of a chain transfer agent containing functional group(s) having 1 to 20 carbon atoms (mercaptopropionic acid, aminoethanethiol, butanethiol, etc.) or a polymerization initiator containing amino and carboxyl groups.

The polymer compound represented by the formula of Group E-1, Group E-2, Group E-3, Group E-4 or Group E-5 according to the present invention can be fixed onto the surface of a carrier (silica gel, polymer gel, etc.) with the use of, for example, a reactive functional group having been introduced into the terminal thereof. Alternatively, the polymer compound can be fixed on the surface of a carrier (silica gel, polymer gel, etc.) by fixing a polymerization initiator on the surface of a solid (silica gel, polymer, etc.), dissolving one or more monomers serving as the starting materials of the polymer compound in a polymerization solvent, and then effecting a polymerization reaction, for example, under heating in the presence of the carrier (silica gel, polymer gel, etc.) having the polymerization initiator fixed thereon. Similar to the above-described case, a bifunctional monomer (i.e., a crosslinking agent) may be dissolved in this step to give a gel structure containing the desired polymer compound. It is also possible to dissolve a chain transfer agent in the polymerization solvent too so as to control the molecular weight of the polymer compound or to introduce a reactive functional group thereinto. Materials containing such a polymer compound are applicable to various liquid chromatographic packings, materials for the separation, adsorption or release of biological components (proteins, peptides, nucleic acids, etc.) and chemicals and biofunctional materials.

EXAMPLES

The present invention will be described in greater detail by reference to the following Examples, but it should be understood that the invention is not construed as being limited thereto.

Example A1

Synthesis of poly-acetamide-propyl methacrylate 0.9 g of 2-N-aminoethyl methacrylate hydrochloride was dissolved in a methanol solvent and 1.0 g of propionic anhydride and 0.9 g of triethylamine (TEA) were added thereto. The resultant mixture was stirred under ice-cooling for 4 hours.

After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify a precursor of the target product acetamide-propyl methacrylate ($CH_3CONH-(CH_2)_3-O-CO-C(CH_3)=CH_2$) (yield: 75%). 0.3 g of this precursor was dissolved in 5 ml of n-propanol and 6.2 mg of 2,2-azobisisobutyronitrile (AIBN) was added thereto. Then, the mixture was polymerized at 75° C. for 12 hours under a nitrogen atmosphere. After the completion of the polymerization, the reaction mixture was ice-cooled and a half of the solvent was removed with an evaporator. The residue was reprecipitated from an acetone solvent and dried in vacuo. Thus, the target product having a molecular weight (Mn) of 3,200, determined by gel permeation chromatography, was obtained. After drying, an aqueous solution of 0.1% by weight of poly-methacryloyl-acetylaminoethyl-ester was prepared and the change in the permeability of the solution depending on temperature was measured (FIG. 1).

Example A2

Synthesis of poly-propionamide-propyl acrylate 4 g of 3-aminopropyl alcohol was dissolved in 100 ml of a dichloromethane solvent and 10 g of propionic anhydride and 0.9 g of triethylamine (TEA) were added thereto. The resultant mixture was stirred at 50° C. for 4 hours. After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify a precursor of the target product propionamide-propyl acrylate ($CH_3CH_2CONH-(CH_2)_3-O-COCH=CH_2$). 1.0 g of this precursor and 8 mg of 2,2-azobis(2-amidinopropane) dihydrochloride were dissolved in 10 ml of ethanol and polymerized at 70° C. for 3 hours. After the completion of the polymerization, an adequate amount of the solvent was removed with an evaporator. The residue was reprecipitated from an alcohol/ethyl acetate/acetone solvent to give poly-propionamide-acrylate. An aqueous solution of 1% by weight of this polymer was prepared and introduced into a thermostat at 90° C. Then, the solution became cloudy. Next, the cloudy solution was ice-cooled. As a result, the solution became transparent. Since these phenomena occurred reversibly, it was confirmed that this polymer showed temperature-responsiveness in the aqueous solution.

Example B1

Synthesis of propionamide-propyl methacrylamide
($CH_3CH_2CONH$—$(CH_2)_3$—$NH$—$CO$—$C(CH_3)$=$CH_2$)

Figure 2:
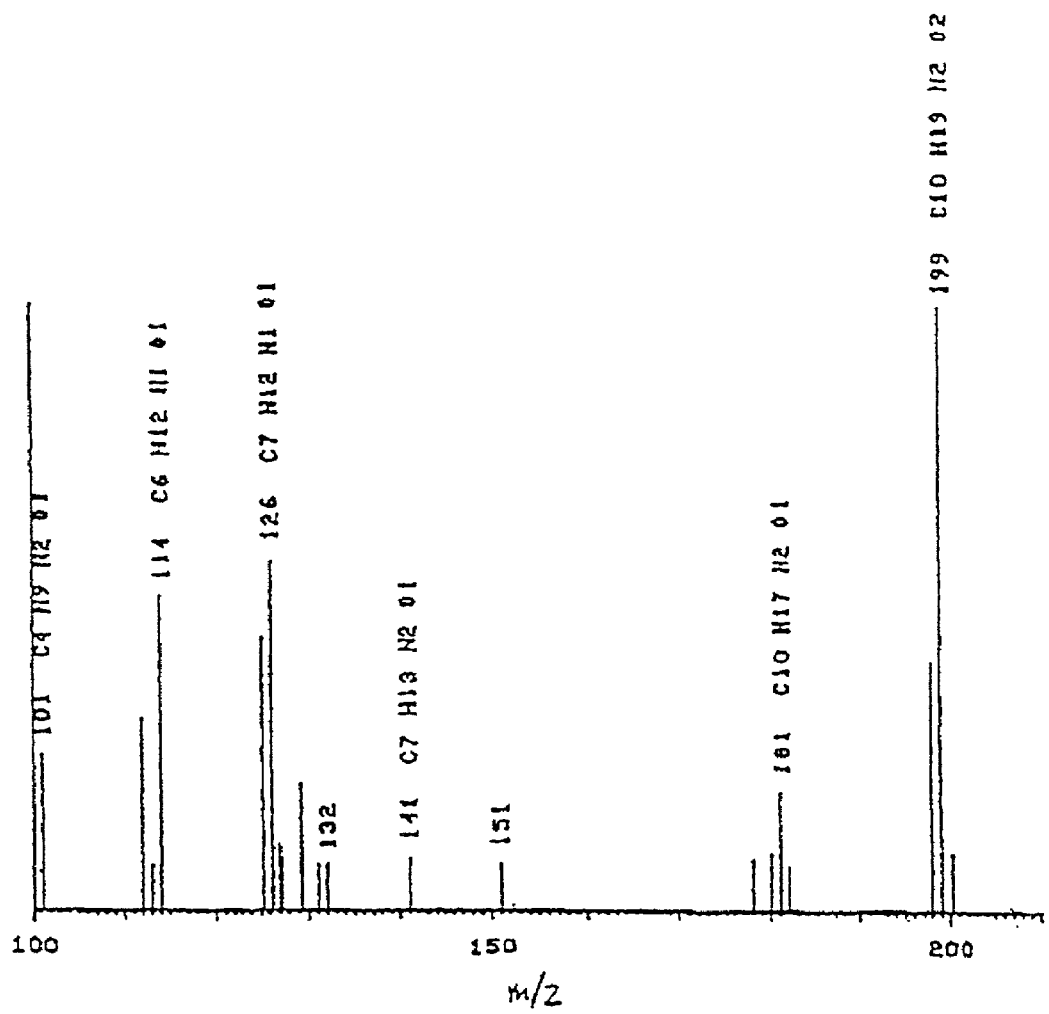
FIG. 2 provides a spectrogram showing the results of mass spectrometric analysis of the purified product obtained in Example B1.
Figure 3:
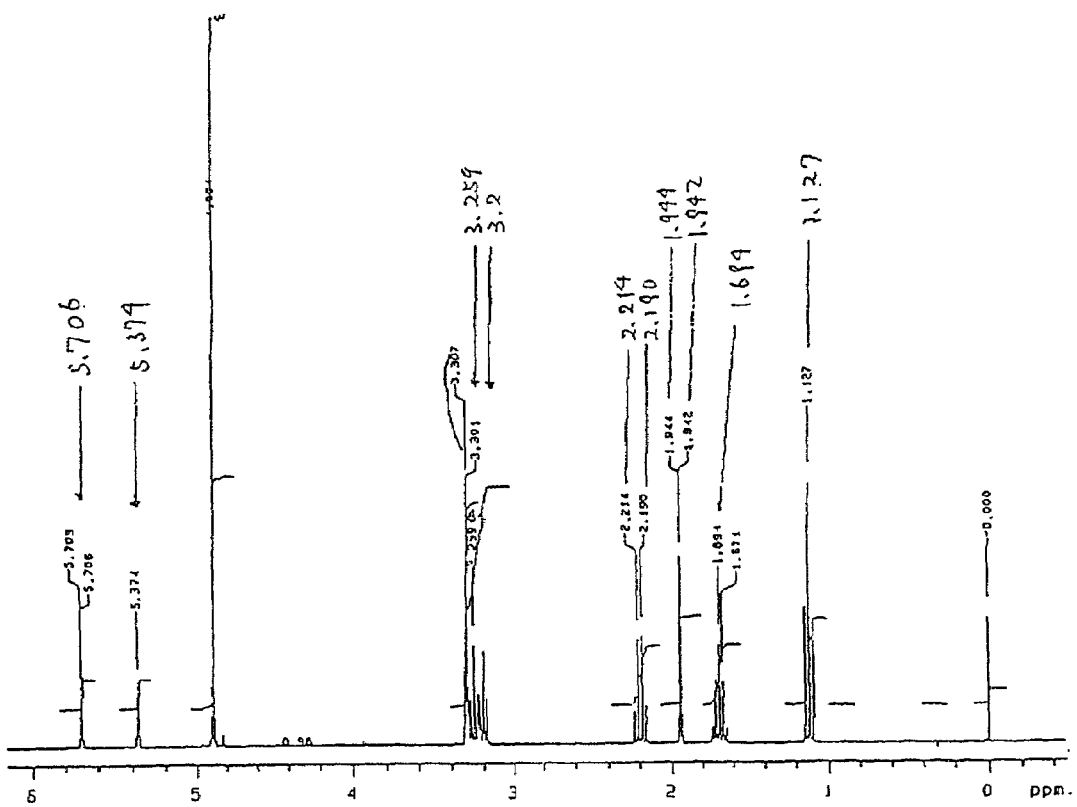
FIG. 3 provides a spectrogram showing the results of $^1$H-NMR analysis of the purified product obtained in Example B1.

0.8 g of 3-aminopropyl methacrylamide hydrochloride was dissolved in a methanol solvent and 1.0 g of propionic anhydride and 0.9 g of triethylamine (TEA) were added thereto. The resultant mixture was stirred under ice-cooling for 4 hours. After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify the target propionamide-propyl methacrylamide (yield: 95%). FIG. 2 shows the result of the mass spectrometry of the purified product while FIG. 3 shows the result of $^1$H-NMR thereof.

Example B2

Synthesis of acetylamide-propyl methacrylamide
($CH_3CONH$—$(CH_2)_3$—$NH$—$CO$—$C(CH_3)$=$CH_2$)

0.8 g of 3-aminopropyl methacrylamide hydrochloride was dissolved in a methanol solvent and 0.9 g of acetic anhydride and 0.9 g of triethylamine (TEA) were added thereto. The resultant mixture was stirred under ice-cooling for 4 hours. After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify the target acetylamide, N-3-propyl methacrylamide (yield: 92%).

Example B3

Synthesis of butyrylamide-propyl methacrylamide
($CH_3(CH_2)_2CONH$—$(CH_2)_3$—$NH$—$CO$—$C(CH_3)$—$CH_2$)

0.8 g of 3-aminopropyl methacrylamide hydrochloride was dissolved in a methanol solvent and 1.5 g of butyric anhydride and 0.9 g of triethylamine (TEA) were added thereto. The resultant mixture was stirred under ice-cooling for 4 hours. After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify the target butyrylamide, N-3-propyl methacrylamide (yield: 92%).

Example B4

Synthesis of propionamide-propyl methacrylamide
($CH_3CH_2CONH$—$(CH_2)_3$—$NH$—$CO$—$CH$=$CH_2$)

5.0 g of 1,3-aminopropyldiamine was mixed with 150 ml of an acetonitrile solvent under ice-cooling. Then, a solution of 6.0 g of acrylic acid chloride dissolved in 60 ml of acetonitrile was slowly dropped thereinto under-ice cooling with stirring for 5 hours. After the completion of the stirring, the precipitate was recovered and dissolved in a TEA/methanol solvent. Then, 3-aminorpopyl acrylamide was purified with a silica column. To the eluate containing this product, 10 g of propionic anhydride was added and the resultant mixture was stirred under-ice cooling. After the completion of the reaction, the solvent was distilled off with an evaporator and the precipitate was filtered off. The filtrate was recovered and introduced into a silica column. Thus, the eluate fraction containing the target product was taken up and subjected to recrystallization to thereby purify the target propionamide-propyl methacrylamide (yield: 75%).

Example B5

Figure 4:
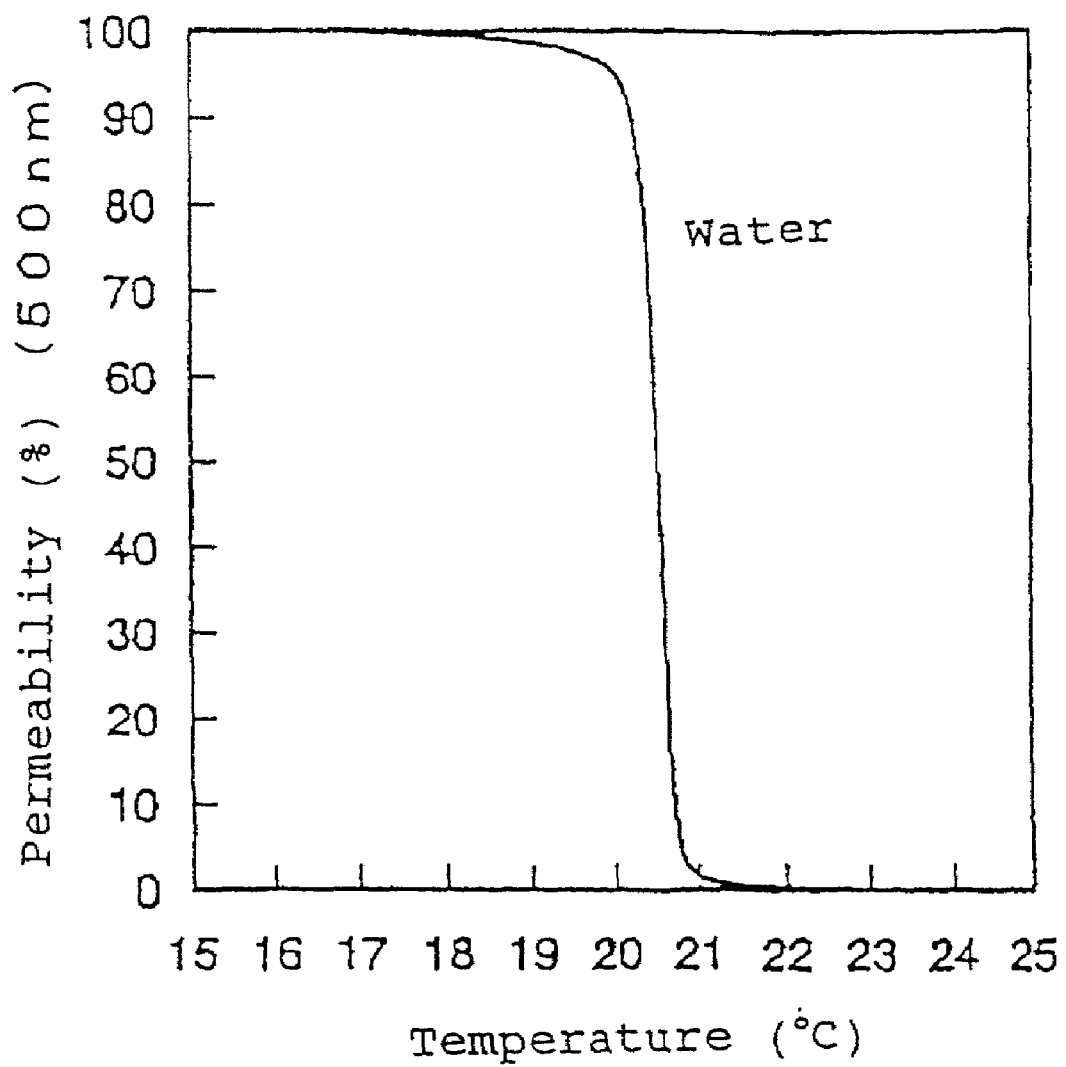
FIG. 4 provides a graph showing a relationship between the permeability and temperature of the polymer obtained in Example B5.

Polymerization of butyrylamide-propylmethacrylamide 0.3 g of the monomer butylamide, N-3-propyl methacrylamide was dissolved in 5 ml of n-propanol. After adding 6.2 mg of 2,2-azobisisobutyronitrile (AIBN), the mixture was polymerized at 75° C. for 12 hours under a nitrogen atmosphere. After the completion of the polymerization, a half of the solvent was removed with an evaporator and the residue was reprecipitated from an acetone solvent and dried in vacuo. Next, an aqueous solution of 1% by weight of polybutylamide and N-3-propylmethacrylamide was prepared and the permeability of the solution was measured at various temperatures. Based on these results, it was confirmed that the polymer showed a cloud point in the aqueous solution. FIG. 4 shows the results.

Example B6

Figure 5:
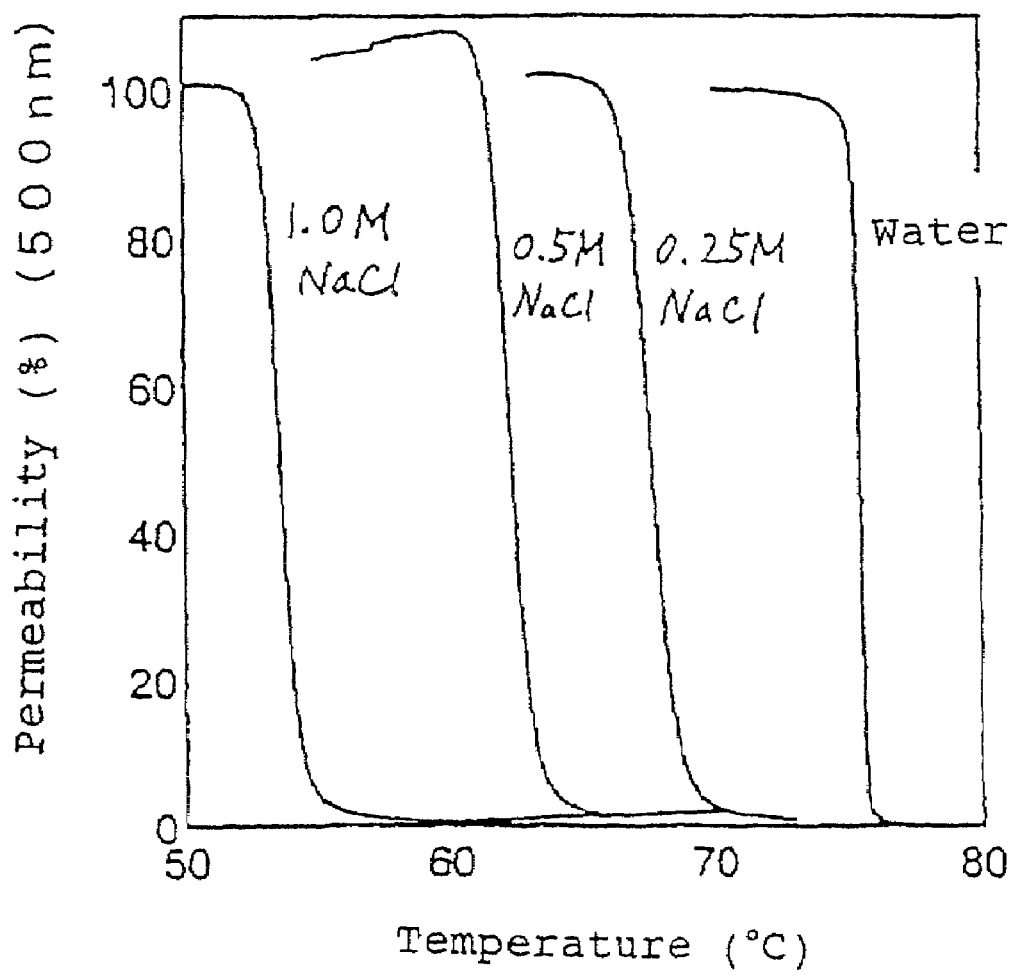
FIG. 5 provides a graph showing a relationship between the permeability and temperature of the polymer obtained in Example B6.

Polymerization of acetylamide-propylmethacrylamide 0.4 g of the monomer acetylamide, N-3-propyl methacrylamide was dissolved in 5 ml of methanol. After adding 6.0 mg of 2,2-azobis(2-amidinopropane) dihydrochloride, the mixture was polymerized at 65° C. for 4 hours under a nitrogen atmosphere. After the completion of the polymerization, the reaction mixture was ice-cooled and a half of the solvent was removed with an evaporator. The residue was reprecipitated from an acetone solvent and dried in vacuo. Next, an aqueous solution of 1% by weight of polyacetylamide and N-3-propyl methacrylamide and NaCl solutions (1.0, 0.5 and 0.25 M) thereof were prepared and the permeabilities of these solutions were measured at various temperatures. Based on these results, it was confirmed that the polymer showed cloud points in the NaCl solutions and the cloud point was lowered with an increase in the salt concentration. FIG. 5 shows the results.

Example B7

Figure 6:
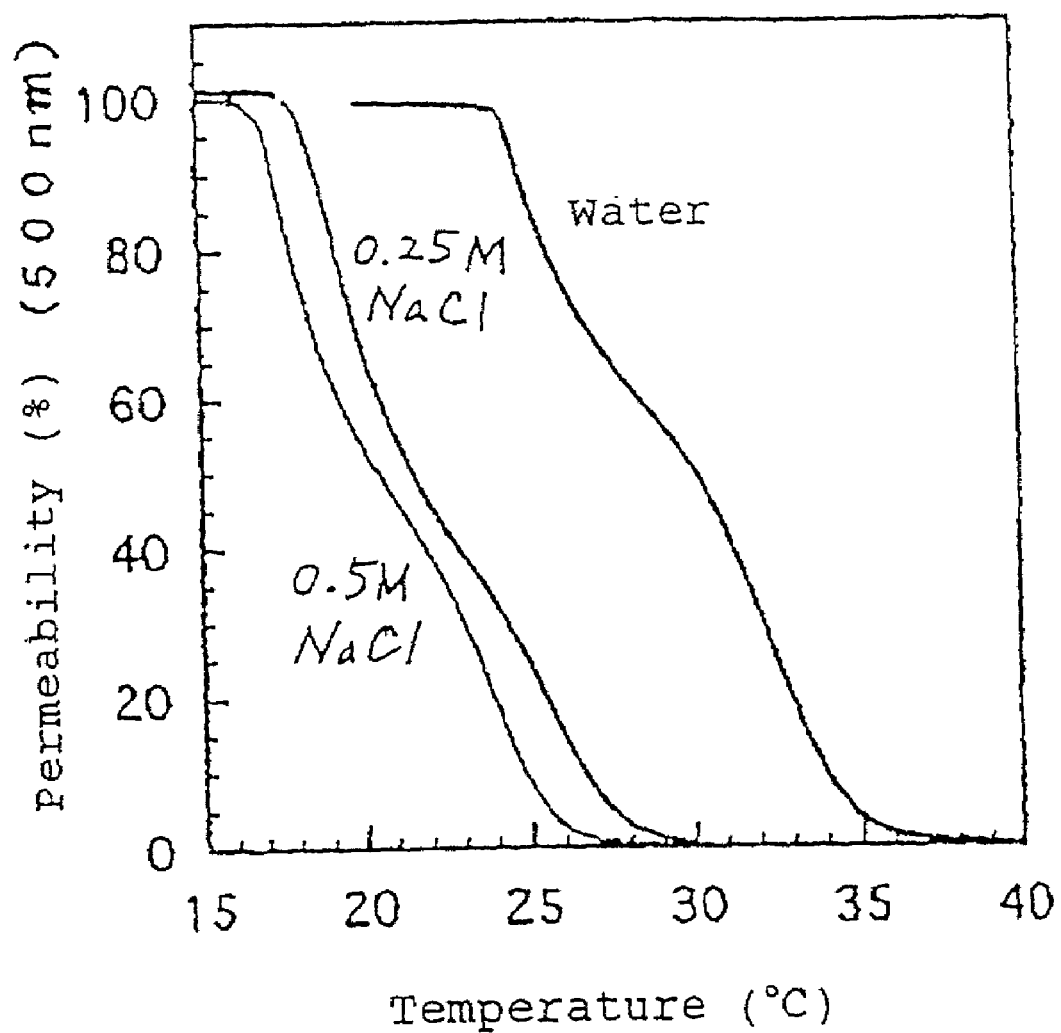
FIG. 6 provides a graph showing a relationship between the permeability and temperature of the polymer obtained in Example B7.

Polymerization of propionamide-propylmethacrylamide 0.7 g of propionamide-propyl methacrylamide was dissolved in 8 ml of methanol. After adding 6.2 mg of 2,2-azobis(2-amidinopropane) dihydrochloride, the mixture was polymerized at 65° C. for 4 hours under a nitrogen atmosphere. After the completion of the polymerization, the reaction mixture was ice-cooled and a half of the solvent was removed with an evaporator. The residue was reprecipitated from an acetone solvent and dried in vacuo. Next, a solution of 1% by weight of polyacetylamide-propyl methacrylamide in a 500 mM aqueous solution of NaCl was prepared and introduced into a thermostat at 70° C. Thus, the solution became cloudy. Next, the cloudy solution was ice-cooled. As a result, the polymer was dissolved. Since these phenomena occurred reversibly, it was confirmed that this polymer had a cloud point. Further, an aqueous solution of 1% by weight of polyacetylamide-propyl methacrylamide and NaCl solutions (0.5 and 0.25 M) thereof were prepared and the permeabilities of these solutions were measured at various temperatures. Based on these results, it was confirmed that the polymer showed cloud points in the NaCl solutions and the cloud point was lowered with an increase in the salt concentration. FIG. 6 shows the results.

Example C1

3-Aminoacetanilide (50 mmol) and triethylamine (56 mmol) were dissolved in dimethylformamide (100 mL) and acryloyl chloride (55 mmol) was dropped thereinto under ice-cooling. After the completion of the addition, the resultant mixture was stirred at room temperature for 2 hours. After filtering off the precipitate, the solvent was distilled off. Then the solid matter thus obtained was recrystallized from a solvent mixture of hexane, ethyl acetate and acetone to give 3-acrylamidoacetanilide at a yield of 61%.

4-Aminoacetanilide (50 mmol) and triethylamine (56 mmol) were dissolved in dimethylformamide (100 mL) and acryloyl chloride (55 mmol) was dropped thereinto under ice-cooling. After the completion of the addition, the resultant mixture was stirred at room temperature for 2 hours. After filtering off the precipitate, the solvent was distilled off. Then the solid matter thus obtained was recrystallized from a solvent mixture of water with methanol to give 4-acrylamidoacetanilide at a yield of 77%.

4-Aminobenzamide (29 mmol) and triethylamine (33 mmol) were dissolved in dimethylformamide (100 mL) and acryloyl chloride (33 mmol) was dropped thereinto under ice-cooling. After the completion of the addition, the resultant mixture was stirred at room temperature for 2 hours. After filtering off the precipitate, the solvent was distilled off. Then the solid matter thus obtained was recrystallized from a solvent mixture of water with methanol to give 4-acrylamidobenzamide at a yield of 60%.

Acrylamide was dissolved in water and subjected to radical polymerization at 70° C. with the use of 2,2'-azobis(2-amidinopropane) dihydrochloride as an initiator to thereby give polyacrylamide as a homopolymer. Hydroxymethyl acrylamide was dissolved in water and subjected to radical polymerization at 70° C. with the use of 2,2'-azobis(2-amidinopropane) dihydrochloride as an initiator to thereby give polyhydroxymethyl acrylamide as a homopolymer. N,N-Dimethyl acrylamide was dissolved in water and subjected to radical polymerization at 70° C. with the use of 2,2'-azobis(2-amidinopropane) dihydrochloride as an initiator to thereby give poly(N,N-dimethyl acrylamide) as a homopolymer. Glycerol monomethacrylate was dissolved in water and subjected to radical polymerization at 70° C. with the use of 2,2'-azobis(2-amidinopropane) dihydrochloride as an initiator to thereby give polyglycerol monomethacrylate as a homopolymer. Glycosyloxyethyl methacrylate was dissolved in water and subjected to radical polymerization at 70° C. with the use of 2,2'-azobis(2-amidinopropane) dihydrochloride as an initiator to thereby give polyglycosyloxyethyl methacrylate as a homopolymer. 3-Acrylamidoacetanilide was dissolved in dimethylformamide and subjected to radical polymerization at 70° C. with the use of azobisisobutyronitrile as an initiator to thereby give poly(3-acrylamidoacetanilide) as a homopolymer. 4-Acrylamidoacetanilide was dissolved in dimethylformamide and subjected to radical polymerization at 70° C. with the use of azobisisobutyronitrile as an initiator to thereby give poly(4-acrylamidoacetanilide) as a homopolymer. 4-Acrylamidobenzamide was dissolved in dimethylformamide and subjected to radical polymerization at 70° C. with the use of azobisisobutyronitrile as an initiator to thereby give poly(4-acrylamidobenzamide) as a homopolymer.

The solubility in water of each of these 8 homopolymers was examined. Although polyacrylamide, polyhydroxymethyl acrylamide, polyglycosyloxyethyl methacrylate, polyglycerol monomethacrylate and poly(N,N-dimethyl acrylamide) were soluble in water, they showed no change in turbidity, etc. with a temperature change, thereby expressing no temperature-responsiveness. On the other hand, poly(3-acrylamidoacetanilide), poly(4-acrylamidoacetanilide) and poly(4-acrylamidobenzamide) were hardly soluble in water and showed no remarkable change in solubility with a temperature change, thereby expressing no temperature-responsiveness.

Example C2

Acrylamide (0.90 or 0.85 mmol), 3-acrylamidoacetanilide (0.1 or 0.15 mmol) and azobisisobutyronitrile (0.05 mmol) were dissolved in a solvent mixture of dimethylformamide (2.5 mL) with dimethyl sulfoxide (2.5 mL) and subjected to radical polymerization at 70° C. After reprecipitating from ether, poly(acrylamide-co-3-acrylamidoacetanilide) was obtained.

Figure 7:
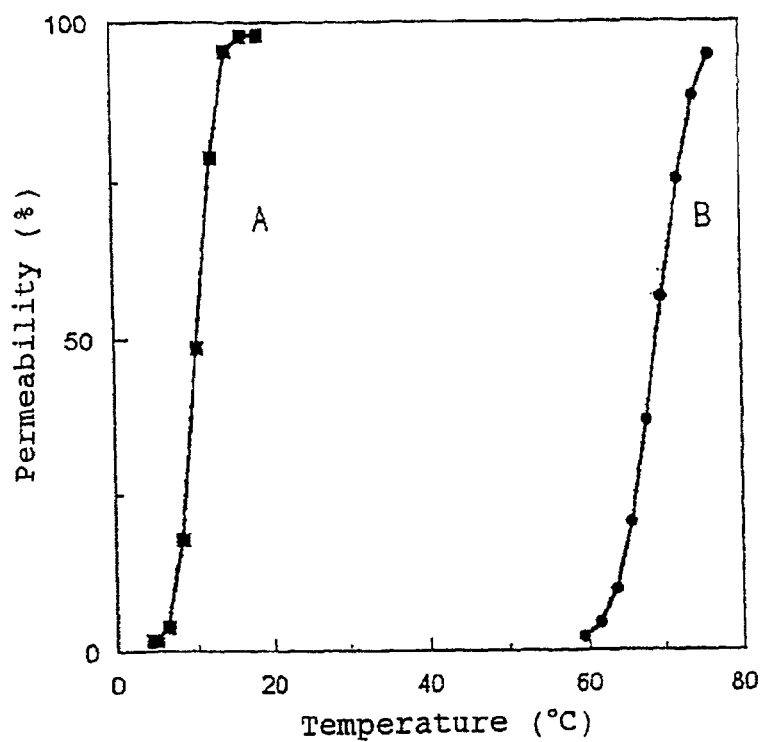
FIG. 7 provides a graph which shows the expression of the temperature-responsiveness by poly(acrylamide-co-3-acrylamideacetanilide) in an aqueous solution obatined in Example C2.

Each copolymer thus obtained was dissolved in water to give a concentration of 1% by weight and a change in the turbidity depending on temperature was observed at 500 nm by using a spectrophotometer. FIG. 7 shows the results. Thus, it was confirmed that the copolymer obtained by feeding acrylamide and 3-acrylamidoacetanilide at a ratio of 90:10 (mol/mol) was a temperature-responsive polymer compound having an UCST of 9° C. while the one obtained by feeding acrylamide and 3-acrylamidoacetanilide at a ratio of 95:15 (mol/mol) was a temperature-responsive polymer compound having an UCST of 69° C. It was also confirmed that the temperature temperature-responsiveness could be changed by altering the feeding ratio.

Further aqueous solutions containing 0.1, 0.5, 1.0 and 3.0% by weight of the copolymer obtained by feeding acrylamide and 3-acrylamidoacetanilide at a ratio of 85:15 were prepared and the UCSTs thereof were measured. As a result, these aqueous solutions respectively showed UCSTs of 32° C., 66° C., 69° C. and 72° C., thus showing that UCST would vary depending on the concentration of the polymer compound too.

Example C3

Acrylamide (0.85 mmol), 3-acrylamidoacetanilide (0.15 mmol), 3-mercaptopropionic acid (10 $\mu$mol, 5 $\mu$mol or 0 $\mu$mol) and 2,2'-azobis(4-cyanovaleric acid) (0.01 mmol) were dissolved in a solvent mixture of dimethylformamide (2.5 mL) with dimethyl sulfoxide (2.5 mL) and subjected to radical polymerization. After reprecipitating from ether, poly(acrylamide-co-3-acrylamidoacetanilide) copolymers with different molecular weights were obtained.

The number-average molecular weights of these copolymers measured by the terminal analysis method were 6500, 9300 and 14200 respectively. Each copolymer was dissolved in water to give a concentration of 1.0% by weight and the temperature-responsiveness was determined. As a result, these copolymers had UCSTs of 26° C., 38° C. and 72° C. respectively. Thus, it was also confirmed that the UCST of a polymer compound could be controlled depending on the molecular weight.

Example C4

Acrylamide (0.85 mmol), 3-acrylamidoacetanilide (0.15 mmol), N,N'-methylenebisacrylamide (0.10 mmol) and 2,2'-azobis(2-amidinopropane) dihydrochloride (0.05 mmol) were dissolved in water (10 mL) and subjected to radical polymerization at 70° C. to give a crosslinked product containing poly(acrylamide-co-3-acrylamidoacetanilide).

Then it was observed whether an aqueous solution of this crosslinked product would undergo a change in turbidity depending on temperature or not. Thus, it was confirmed that the crosslinked product was a temperature-responsive one having an UCST which was cloudy under ice-cooling and soluble at 90° C.

Example C5

Acrylamide (0.8 mmol), 4-acrylamidoacetanilide (0.2 mmol) and 2,2'-azobis (2-amidinopropane) dihydrochloride (0.05 mmol) were dissolved in water (5 mL) and subjected to radical polymerization at 70° C. to give poly(acrylamide-co-4-acrylamidoacetanilide).

Then the polymer compound was dissolved in water and a change in the turbidity thereof depending on temperature was observed. Thus, it was confirmed that this polymer compound was a temperature-responsive one having an UCST which was cloudy under ice-cooling and soluble at 90° C.

Example C6

N,N-Dimethyl acrylamide (0.9 mmol), 3-acrylamidoacetanilide (0.1 mmol) and 2,2'-azobis(2-amidinopropane) dihydrochloride (0.05 mmol) were dissolved in water (5 mL) and subjected to radical polymerization at 70° C. to give poly(N,N-dimethylacrylamide-co-4-acrylamidoacetanilide).

Then the polymer compound was dissolved in water and a change in the turbidity thereof depending on temperature was observed. Thus, it was confirmed that this polymer compound was a temperature-responsive one having an UCST which was soluble under ice-cooling and cloudy at 90° C.

Example C7

Hydroxymethyl acrylamide (0.87 mmol), 3-acrylamidoacetanilide (0.13 mmol) and 2,2'-azobis(2-amidinopropane) dihydrochloride (0.05 mmol) were dissolved in water (5 mL) and subjected to radical polymerization at 70° C. to give poly(hydroxymethylacrylamide-co-3-acrylamidoacetanilide).

Then the polymer compound was dissolved in water and a change in the turbidity thereof depending on temperature was observed. Thus, it was confirmed that this polymer compound was a temperature-responsive one having an UCST which was cloudy under ice-cooling and soluble at 90° C.

Example C8

Acrylamide (0.85 mmol), 4-acrylamidobenzamide (0.15 mmol) and 2,2'-azobis(2-amidinopropane) dihydrochloride (0.05 mmol) were dissolved in a solvent mixture of dimethylformamide (2.5 mL) with dimethyl sulfoxide (2.5 mL) and subjected to radical polymerization at 70° C. to give poly(acrylamide-co-4-acrylamidobenzamide).

Then the polymer compound was dissolved in water to give a concentration of 3.0% by weight and temperature was changed. As a result, it was found out that this compound was a temperature-responsive polymer compound having an UCST of 46° C. Since an aqueous solution (3.0% by weight) of the copolymer obtained by feeding acrylamide and 3-acrylamidoacetanilide at a ratio of 85:15 showed an UCST of 72° C., it was found out that the temperature-responsiveness was affected by functional groups.

Example C9

Glycerol monomethacrylate (0.7 mmol), 4-acrylamidobenzamide (0.3 mmol) and 2,2'-azobis(2-amidinopropane) dihydrochloride (0.05 mmol) were dissolved in water (5 mL) and subjected to radical polymerization at 70° C. to give poly(glycerol monomethacrylate-co-4-acrylamido-benzamide).

Then the polymer compound was dissolved in water and a change in the turbidity thereof depending on temperature was observed. Thus, it was confirmed that this polymer compound was a temperature-responsive one having an UCST which was cloudy under ice-cooling and soluble at 90° C.

Example C10

Glycosyloxyethyl methacrylate (7.7 mmol), 4-acrylamidobenzamide (5.1 mmol), 3-mercaptopropionic acid (0.4 mmol) and 2,2'-azobis(4-cyanovaleric acid) (0.3 mmol) were dissolved in dimethylformamide (30 mL). After subjected to radical polymerization at 70° C. and reprecipitating from dioxane, poly(glycosyloxyethyl methacrylate-co-4-acrylamidebenzamide) was obtained. It was confirmed that the copolymer had a number-average molecular weight of 8000 by measuring by GPC (gel permeation chromatograph) with the use as a mobile phase of dimethylformamide containing 10 mM of lithium bromide. Also, it was confirmed that the copolymer had a number-average molecular weight of 7000 by the terminal analysis method by using 10 mM sodium hydroxide. Moreover, it was confirmed that this polymer compound carried a terminal carboxyl group which was a reactive functional group. It was also confirmed by 1H-NMR that the copolymer compound obtained above contained repeating units of glycosyloxyethyl methacrylate and 4-acrylamido-benzamide at a composition ratio of 62:38 (mol/mol).

Figure 8:
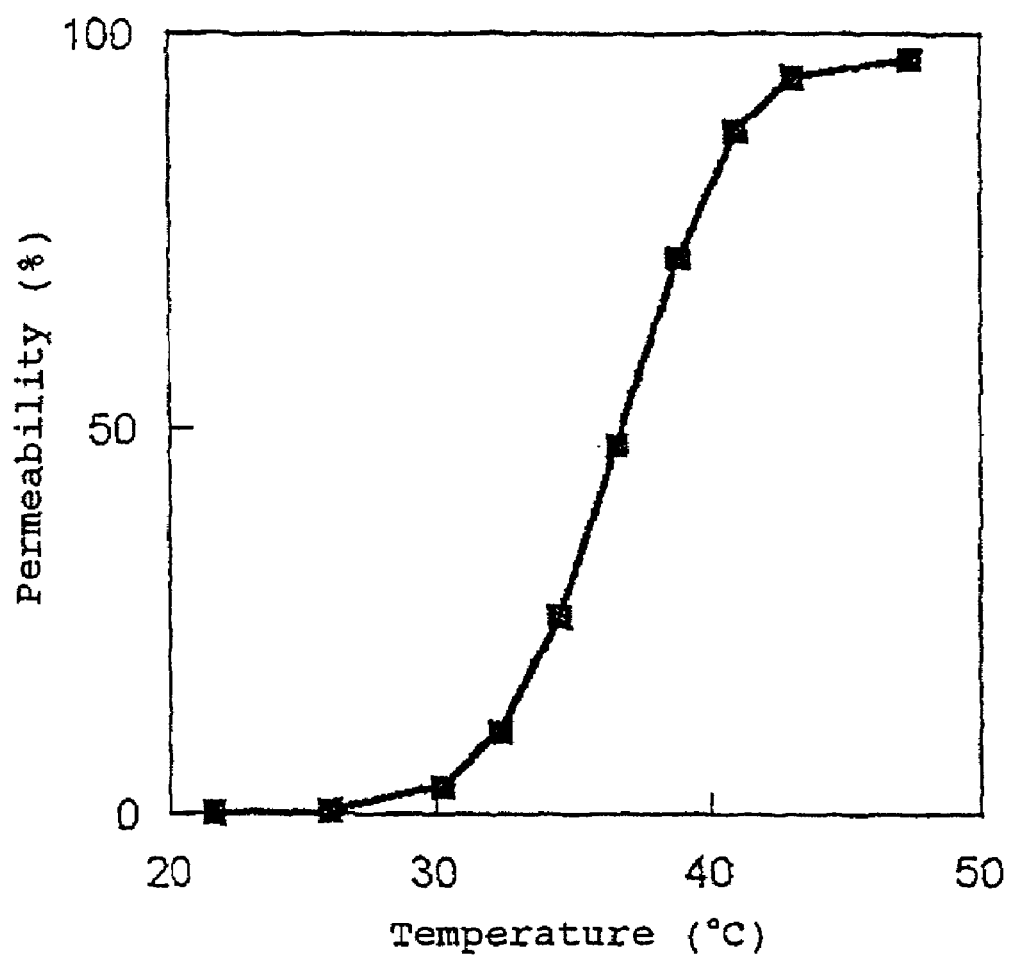
FIG. 8 provides a graph which shows the expression of the temperature-responsiveness by poly(glycosyloxyethylmethacrylate-co-4-acrylamidebenzamide) in an aqueous solution obtained in Example C10.
Figure 9:
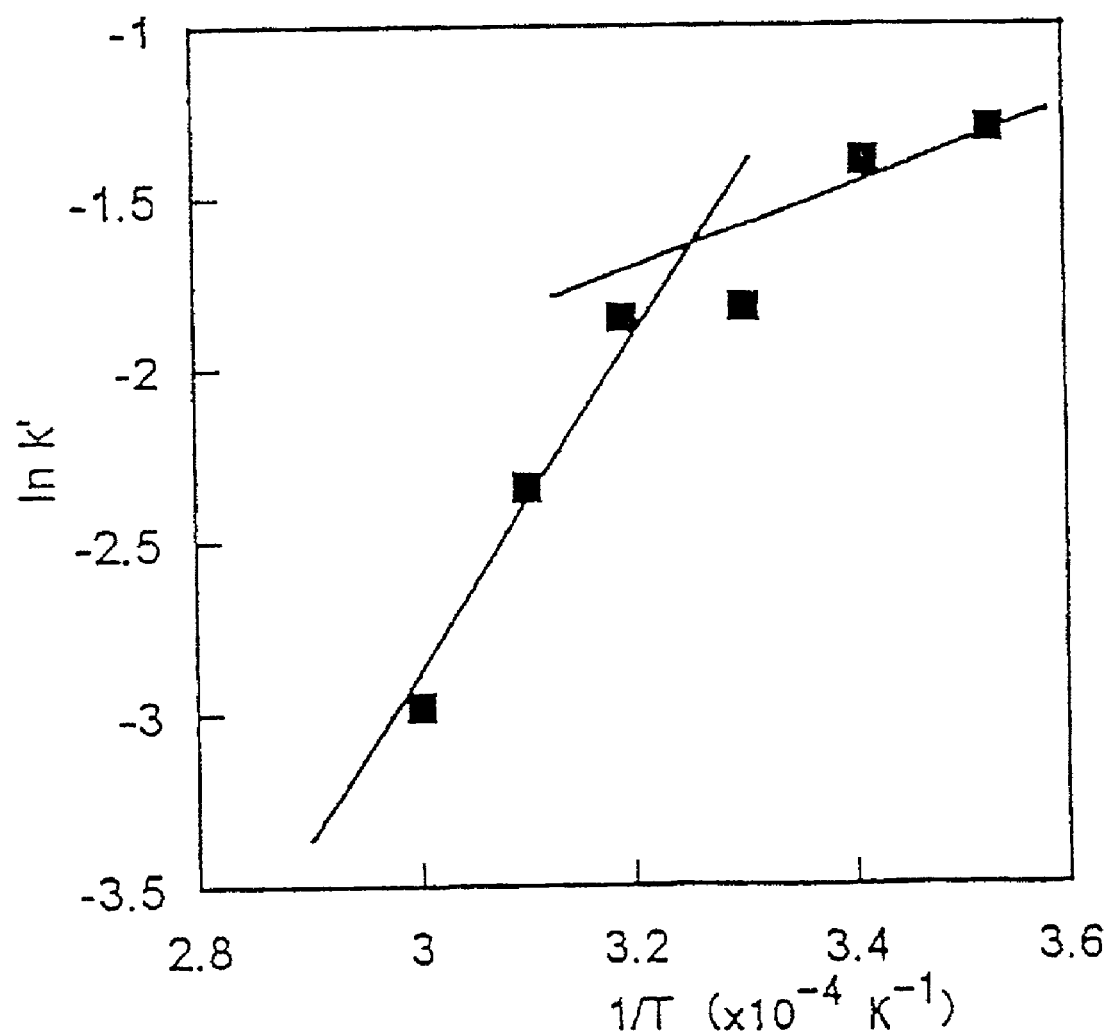
FIG. 9 provides a graph which shows Vant 'Hoff plot of cortisone acetate by silica gel carrying poly(glycosyloxyethylmethacrylate-co-4-acrylamidebenzamide) fixed thereto obtained in Example C10.

The copolymer thus synthesized was dissolved in water and a change in the turbidity thereof depending on temperature was observed at 500 nm by using a spectrophotometer. FIG. 8 shows the results. Thus it was confirmed that this copolymer was also a temperature-responsive polymer compound having an UCST of 35° C.

The polymer thus synthesized (0.8 g) and a condensing agent EEDQ (30 mg) were dissolved in dimethylformamide (15 mL). To the obtained solution, aminopropylsilyl silica gel (0.8 g) was added and the resultant mixture was stirred for 24 hours to thereby fix the copolymer on the silica gel. This silica gel was packed into a stainless steel column having an inner diameter of 4.6 mm and a height of 30 mm.

Figure 10:
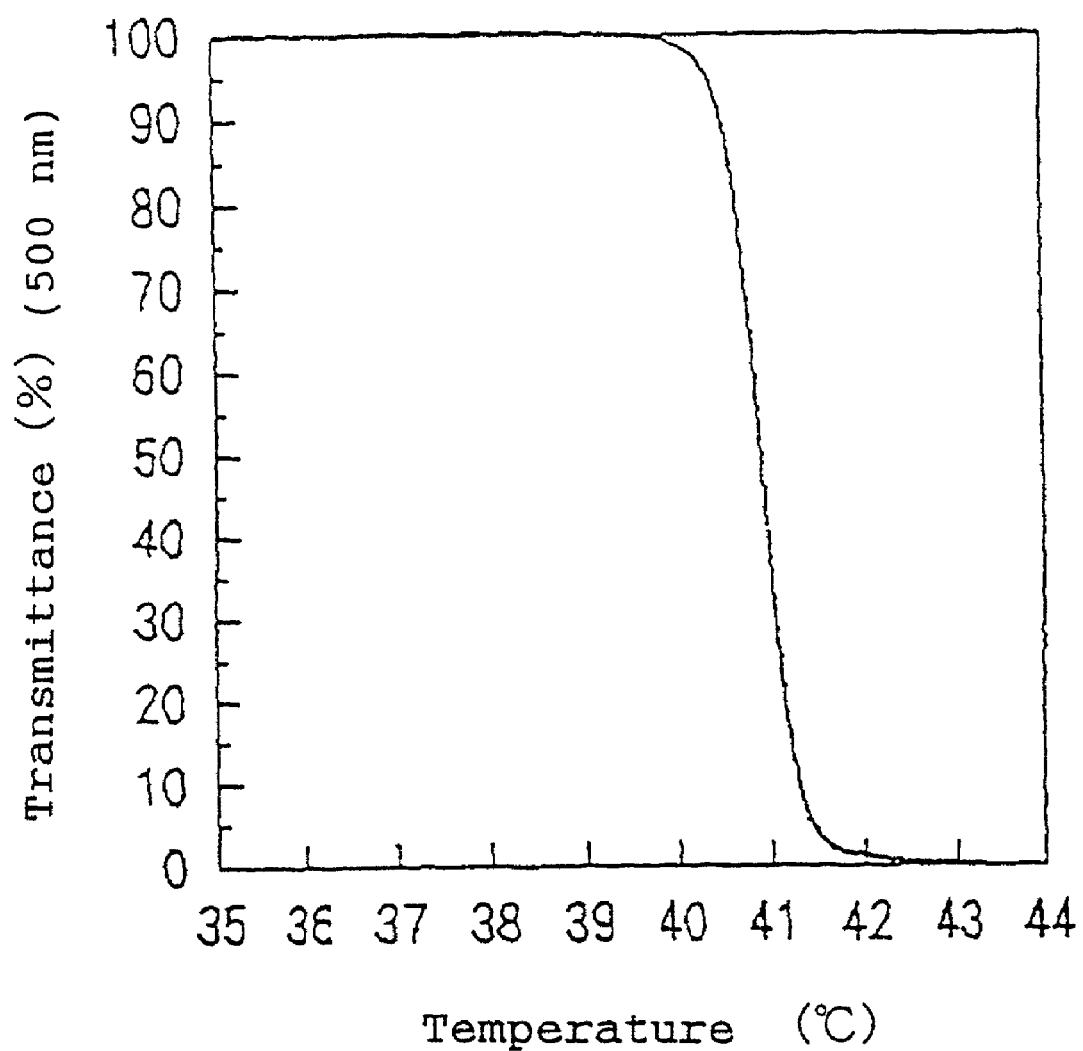
FIG. 10 provides a graph showing the expression of the temperature-responsiveness of poly(5-hydroxypentylacrylamide) in an aqueous solution obtained in Example D1.

By using water as a mobile phase, the relative retentions of cortisone acetate in this column were determined at various temperatures. FIG. 10 shows the results. The slope of the graph shows a large change at around 35° C., which indicates that the copolymer underwent a structural change at around this temperature and thus the retention of the solute (i.e., cortisone acetate) was affected thereby. Thus, it has been found out that the elution behaviors of the solute can be controlled by using the above-described copolymer as a separation material such as a chromatographic support.

Example C11

Acrylic acid (20 g) and 1-ethyl-3-(3-dimethylaminopropyl)carbodiimide (30 g) were dissolved in water (300 mL). Then aminohydroxybutyric acid (2.0 g) was added to the obtained solution and reacted at room temperature for 10 hours. After the completion of the reaction, water was distilled off and the residue was sufficiently washed with hexane (200 mL) in 3 portions. Next, this residue was dissolved in dimethyl-formamide (350 mL), in which N-hydroxysuccinimide (3 g) and N,N'-dicyclohexylcarbodiimide (3 g) had been dissolved, and reacted overnight. After the completion of the reaction, the solvent was distilled off. Ethyl acetate was added to the residue thus obtained and the precipitate thus formed was filtered off. The filtrate was recovered and a fraction containing the target product was taken up by silica gel column chromatography with the use of ethyl acetate as a mobile phase and alumina column chromatography. Next, a half of the solvent was distilled off with an evaporator and recrystallization was carried out by adding a hexane solvent at −20° C. to thereby give the target monomers (N-propylacetamide, N-propyl acrylamide) (yield: 68%).

N-Propylacetamide and N-propyl acrylamide (0.8 g) and 2,2'-azobis(4-cyanovaleric acid) (3 mg) were dissolved in dimethylformamide (8 mL). After purging with nitrogen, the mixture was polymerized in a sealed container at 65° C. for 4 hours. After the completion of the reaction, the solvent was distilled off and the residue was reprecipitated from acetone to give poly(N-propylacetamide, N-propyl acrylamide) (yield: 83%).

Then this polymer compound was dissolved in water and a change in the turbidity thereof depending on temperature was observed. Thus, it was confirmed that this polymer compound was a temperature-responsive one having an LCST which was soluble under ice-cooling and cloudy at 90° C.

Example D1

5-Aminopentanol (5.4 g) and triethylamine (5.6 ml) were added to dimethylformamide (140 ml). Into the resultant solution, a solution of acrylic acid chloride (4.2 ml) in dimethylformamide (30 ml) was dropped at −40° C. under stirring. After 2 hours, the solution was filtered and the precipitate was eliminated. Next, the solvent was eliminated with the use of a rotary evaporator. After the elimination of the solvent, the residue was dissolved in acetone and an eluate containing the target product was taken up with the use of a silica gel column. Then the solvent was eliminated with a vacuum pump to purify 5-hydroxypentylacrylamide (2.1 g).

The obtained 5-hydroxypentylacrylamide (1.0 g) and 4,4'-azobis(4-cyanovaleric acid) (20 mg) employed as a polymerization initiator were added to dimethylformamide (5 ml). After degassing by the freezing-thawing method, radical polymerization was carried out at 65° C. for 3 hours. After the completion of the polymerization reaction, dimethyl sulfoxide (7 ml) was added to the liquid reaction mixture. The obtained mixture was subjected to re-precipitation in a mixture of acetone/ether (volume ratio: 1:3) to thereby give the target homopolymer of poly(5-hydroxypentylacrylamide) (0.51 g). The number-average molecular weight (Mn) of the obtained polymer was 20,000 and the molecular weight distribution (Mw/Mn) thereof was 2.77.

This homopolymer was dissolved in an aqueous solution to give a concentration of 0.1% by weight. Then the change in transmittance with a change in temperature was monitored (FIG. 10). Thus, it was indicated that the cloud point of this polymer was about 40.8° C.

To fix this polymer on a chromatographic packing, this polymer (0.3 g), hydroxysuccinimide (0.8 g) and dicyclohexylcarbodiimide (0.8 g) were dissolved in dimethylformamide (30 ml) and stirred at room temperature overnight. After the completion of stirring, the precipitate thus formed was sufficiently removed and re-precipitation was effected in a solvent mixture of acetone/diethyl ether (volume ratio: 1:3). After vacuum-drying, the desired polymer carrying a hydroxysuccinimide group at the polymer terminal was obtained. Next, this activated polymer (0.15 g) and aminopropyl silica (0.75 g) were added to dimethylformamide (30 ml) and thus the polymer was fixed on the silica. After the fixation, the above procedure was repeated under the same conditions to thereby fix the polymer. The elemental analysis data indicated that the organic matter content was increased by 10% by weight, which proved that the polymer had been fixed.

This silica was packed in a stainless column (4.6×30 mm) and peptides were separated by using the same. As a result, it was proved that the retention times of peptides (β-endorphin, angioten, etc.) in an aqueous mobile phase varied depending on temperature.

Example D2

Trans-aminocyclohexanol (5.0 g) and triethylamine (6.1 ml) were added to chloroform (100 ml). Into the obtained mixture, a solution of acrylic acid chloride (3.4 ml) in chloroform (30 ml) was dropped under ice-cooling over 2 hours, thus effecting a reaction. After the completion of the dropping/reaction, the resultant mixture was stirred at room temperature for 1 hour. Subsequently, the solvent was eliminated by using a rotary evaporator. After the elimination of the solvent, ethyl acetate (250 ml) was added to the residue and the precipitate thus formed was filtered off. Next, the filtrate was treated with a silica column and an eluate containing the target product was taken up. After concentrating, n-hexane (250 ml) was added thereto followed by recrystallization, filtration and drying, thus giving the target 4-hydroxycyclohexylacrylamide (2.4 g).

Figure 11:
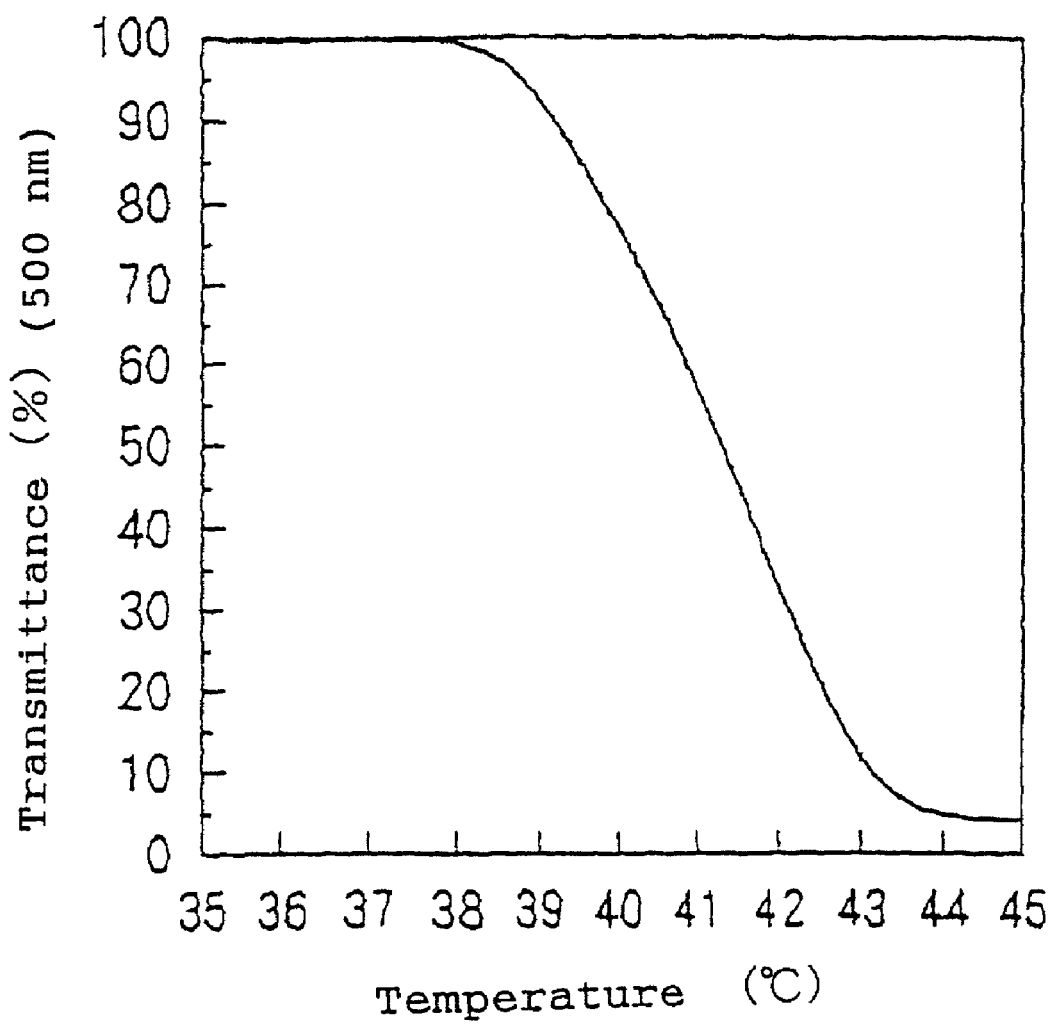
FIG. 11 provides a graph showing the expression of the temperature-responsiveness of poly(trans-hydroxycyclohexylacrylamide) in an aqueous solution obtained in Example D2.

This monomer (0.8 g) and 4,4'-azobis(4-cyanovaleric acid) (5 mg) employed as a polymerization initiator were added to dimethylformamide (5 ml). After degassing by the freezing-thawing method, polymerization was carried out at 65° C. for 3 hours. After the completion of the polymerization, dimethyl sulfoxide (7 ml) was added to the liquid reaction mixture. The obtained mixture was subjected to re-precipitation in a mixture of acetone/diethyl ether (volume ratio: 1:3) followed by vacuum-drying to thereby give the target homopolymer of poly(trans-hydroxycyclohexylacrylamide) (0.90 g). Based on the GPC data, the number-average molecular weight (Mn) of the obtained polymer was estimated as 28,000 and the molecular weight distribution (Mw/Mn) thereof was 2.68. By monitoring the transmittance with a change in temperature (FIG. 11), it was clarified that the cloud point of this polymer was about 41.2° C. The number average molecular weight determined by the terminal titration method was also the same as the value described above.

Example D3

5-Hydroxypentylacrylamide (1.0 g), t-butylacrylamide (0.12 g) and 2,2'-azobisisobutyronitrile (12 mg) were dissolved in dimethyl sulfoxide (6 ml) and polymerization was carried out at 70° C. for 3 hours. After the completion of the polymerization reaction, the reaction mixture was added to a mixture of acetone/ether (volume ratio: 1:3) to give the target copolymer. This copolymer was dissolved in an aqueous solution to give a concentration of 1% by weight and then observation was made while changing temperature to examine whether it showed a cloud point or not. As a result, this polymer was dissolved under ice-cooling but became cloudy at 90° C., thus showing a cloud point.

Example D4

6-Aminohexanol (2.0 g) and triethylamine (2.1 mg) were dissolved in a chloroform solvent (80 ml). Into the obtained solution, a solution of acrylic acid chloride (1.4 ml) in chloroform (20 ml) was dropped under ice-cooling over 3 hours. After the completion of the addition, the mixture was stirred at room temperature for 3 hours. After eliminating the solvent with the use of an evaporator, a precipitate was obtained. Then ethyl acetate (120 ml) was added thereto and the precipitate was filtered off. The filtrate was concentrated by using an evaporator and then treated with a silica column to take up an eluate containing the target product followed by concentration and recrystallization to give the desired 6-hydroxy-hexyl-acrylamide (1.4 g). This 6-hydroxyhexyl-acrylamide (1.0 g) and 2,2'-azobisisobutylnitrile (10 mg) employed as a polymerization initiator were dissolved in dimethylformamide (5 ml). After degassing by the freezing-thawing method, polymerization was carried out at 70° C. for 2 hours. After the completion of the polymerization, the polymer was re-precipitated by using a solvent mixture tetrahydro-furan/ether (1:1) followed by vacuum-drying to give the target poly(6-hydroxyhexylacrylamide) (0.84 g). Based on the GPC data, the number-average molecular weight (Mn) of the obtained polymer was estimated as 9,600 and the molecular weight distribution (Mw/Mn) thereof was 4.05.

Figure 12:
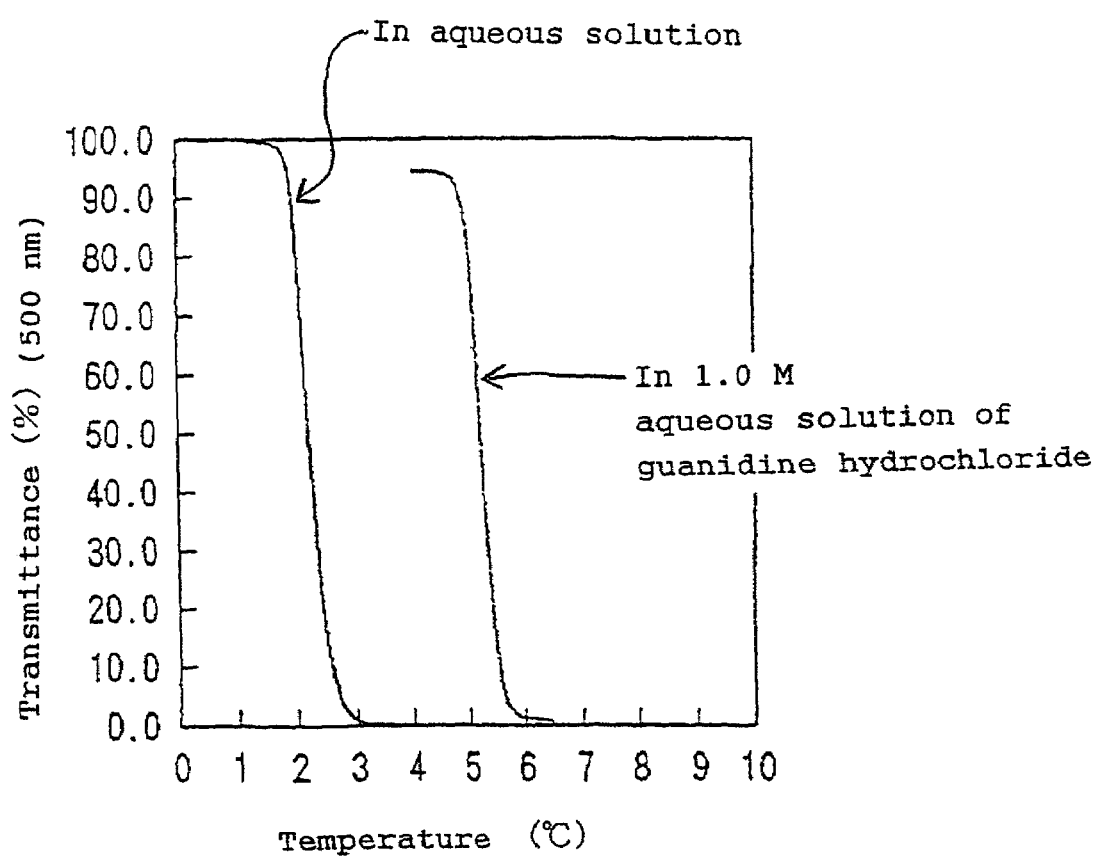
FIG. 12 provides a graph showing the expression of the temperature-responsiveness of poly(6-hydroxyhexylacrylamide) in aqueous solutions obtained in Example D4.

This polymer was dissolved in an aqueous solution to give a concentration of 1% by weight and the change in transmittance was monitored while changing temperature (FIG. 12). To examine the temperature-responsiveness in an aqueous solution of guanidine, the polymer was dissolved in a 1.0 M aqueous solution of guanidine hydrochloride to give the same concentration and the change in transmittance was monitored while changing temperature. As a result, it was clarified that this polymer showed a cloud point at 2.1° C. in the aqueous solution and at 5.2° C. in the 1.0 M aqueous solution of guanidine hydrochloride.

Example D5

5-Hydroxypentylacrylamide (0.8 g), acrylamide (0.2 g) and 2,2'-azobizisobutylnitrile (10 mg) were dissolved in dimethyl sulfoxide (7 ml) and polymerization was performed at 70° C. for 2 hours. After the completion of the polymerization reaction, the mixture was added to a solvent mixture of acetone/ether (volume ratio: 1:3) to give the target copolymer. This copolymer was dissolved in an aqueous solution to give a polymer concentration of 1% by weight. Then, observation was made while changing temperature to examine whether it showed a cloud point or not. As a result, this polymer was dissolved under ice-cooling but became cloudy at 90° C., thus showing a cloud point.

Example E1

N-Methacryloyl-N'-benzoyl-1,3-diaminopropane (2.8 mg), N-acryloyl-N'-4-piperidinecarboxamide (6.1 mg) and 2,2'-azobis(1-amidinopropane) dihydrochloride (7 mg) were dissolved in water (1 ml) and subjected to radical polymerization at 80° C. to give a copolymer. Then, this polymer was dissolved in water and the change in turbidity was monitored while changing temperature. As a result, it was cloudy under ice-cooling but dissolved at 90° C., which indicated that it was a temperature-responsive polymer having the UCST. When guanidine hydrochloride was added to this aqueous solution, the phenomenon of the UCST disappeared.

Example E2

N-Methacryloyl-N'-hexanoyl-1,3-diaminopropane (4.7 mg), N-acryloyl-N'-4-piperidinecarboxamide (20.1 mg) and 2,2'-azobis(1-amidinopropane) dihydrochloride (4.8 mg) were dissolved in water (2.5 ml) and subjected to radical polymerization at 80° C. to give a copolymer. Then, this polymer was dissolved in water and the change in turbidity was monitored while changing temperature. As a result, it was dissolved under ice-cooling but cloudy at 90° C., which indicated that it was a temperature-responsive polymer having the UCST.

Example E3

Into a liquid reaction mixture of 4-piperidinecarboxamide (5.0 mg) and triethylamine (5.3 ml) in dimethylformamide (70 ml), a solution of acrylic acid (3.2 ml) dissolved in dimethylformamide (20 ml) was dropped under ice-cooling over 3 hours. After the completion of the addition, the resultant mixture was stirred at room temperature for 1 hour and then filtered. From the filtrate thus obtained, the solvent was eliminated by using a rotary evaporator. After adding an acetone solution to the residue, the mixture was treated with a silica gel column to give N-acryloyl-4-piperidinecarboxamide (1.4 g).

N-Acryloyl-4-piperidinecarboxamide (0.94 g) and 2,2'-azobis(4-cyanovaleric acid) (50 mg) were dissolved in dimethylformamide (6 ml) and polymerized at 70° C. Subsequently, the reaction mixture was re-precipitated in a solvent mixture of ethanol/diethyl ether (1:4) and the precipitate was taken up by filtration and vacuum-dried. Thus, the target poly(4-piperidinecarboxamide) (0.92 g) was obtained.

This polymer was dissolved in a 200 mM aqueous solution of ammonium sulfate, a 300 mM aqueous solution of ammonium sulfate and a 500 mM aqueous solution of ammonium sulfate each to give a polymer concentration of 1% by weight and changes in turbidity with temperature change (FIG. 13) and changes in turbidity under elevating and lowering temperature (FIG. 14) were compared. Thus, it was confirmed that this polymer showed the UCST in the aqueous ammonium sulfate solutions. It was also found that the UCST shifted toward the high temperature side with an increase in the salt concentration. Next, this polymer (0.9 g) was treated with hydroxysuccinimide (0.6 g) and dicyclohexylcarbodiimide (0.5 g) in a solvent mixture of dimehtylsulfoxide (10 ml) with dimethylformamide (10 ml) to thereby introduce hydroxysuccinimide into the polymer chain terminal. Then it was fixed onto an aminopropyl silica gel. The elemental analysis data indicated that the organic matter content was increased by 13.1% by weight. This silica gel was packed into a stainless column. By using a 500 mM aqueous solution of ammonium sulfate as a mobile phase, insulin β-chain (2 μg) employed as a biological component model was injected into the column. Thus, it was clarified that the elution time varied depending on temperature.

Example E4

Acrylamide (22 mmol), 3-acrylamide acetanilide (3.9 mmol), 3-mercaptopropionic acid (0.3 mmol) and 2,2'-azobis(4-cyanovaleric acid) (0.2 mmol) were dissolved in dimethylformamide (14 ml) and subjected to radical polymerization at 70° C. After re-precipitating in ether, poly(acrylamide-co-3-acrylamide acetanilide) was obtained.

Figure 13:
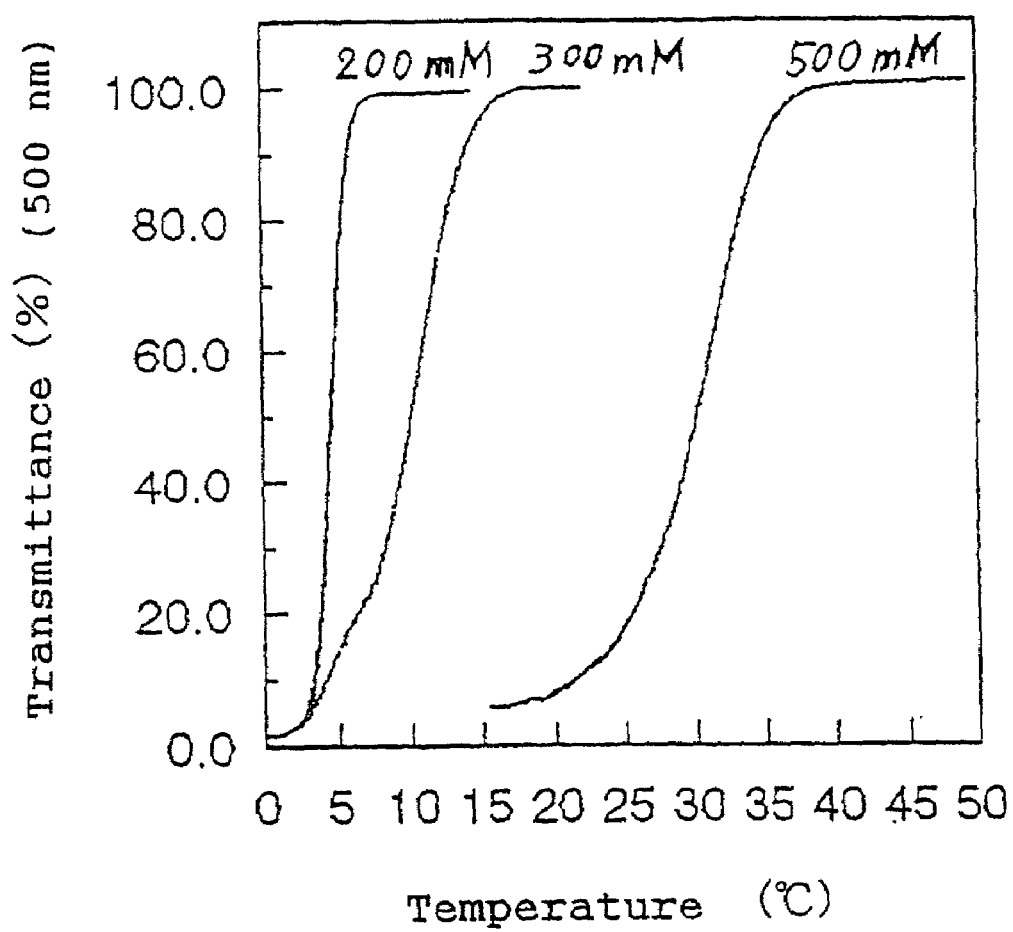
FIG. 13 provides a graph showing the expression of the temperature-responsiveness of poly(4-piperidinecarboxamide) in ammonium sulfate solutions obtained in Example E3.
Figure 14:
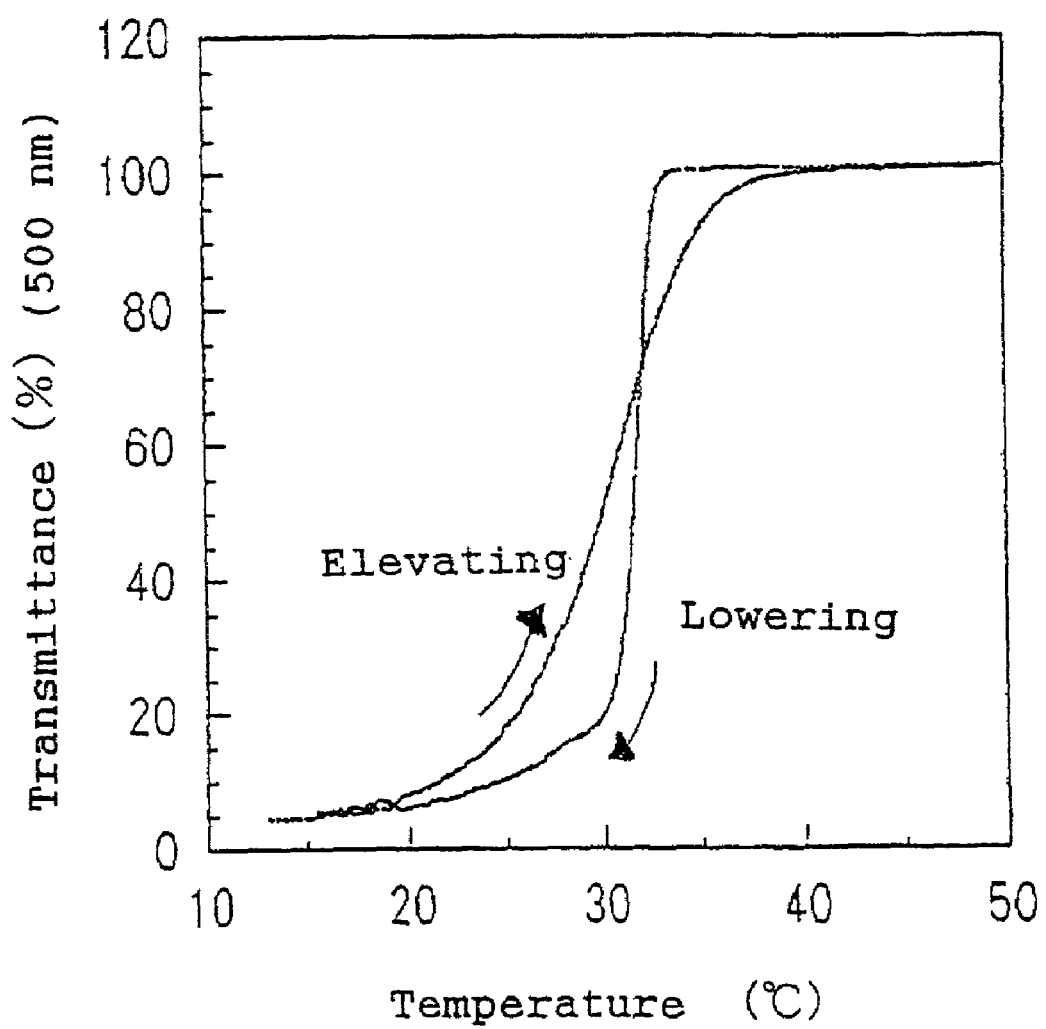
FIG. 14 provides a graph showing the expression of the temperature-responsiveness of poly(4-piperidinecarboxamide) in an ammonium sulfate solution under elevating and lowering temperature obtained in Example E3.
Figure 15:
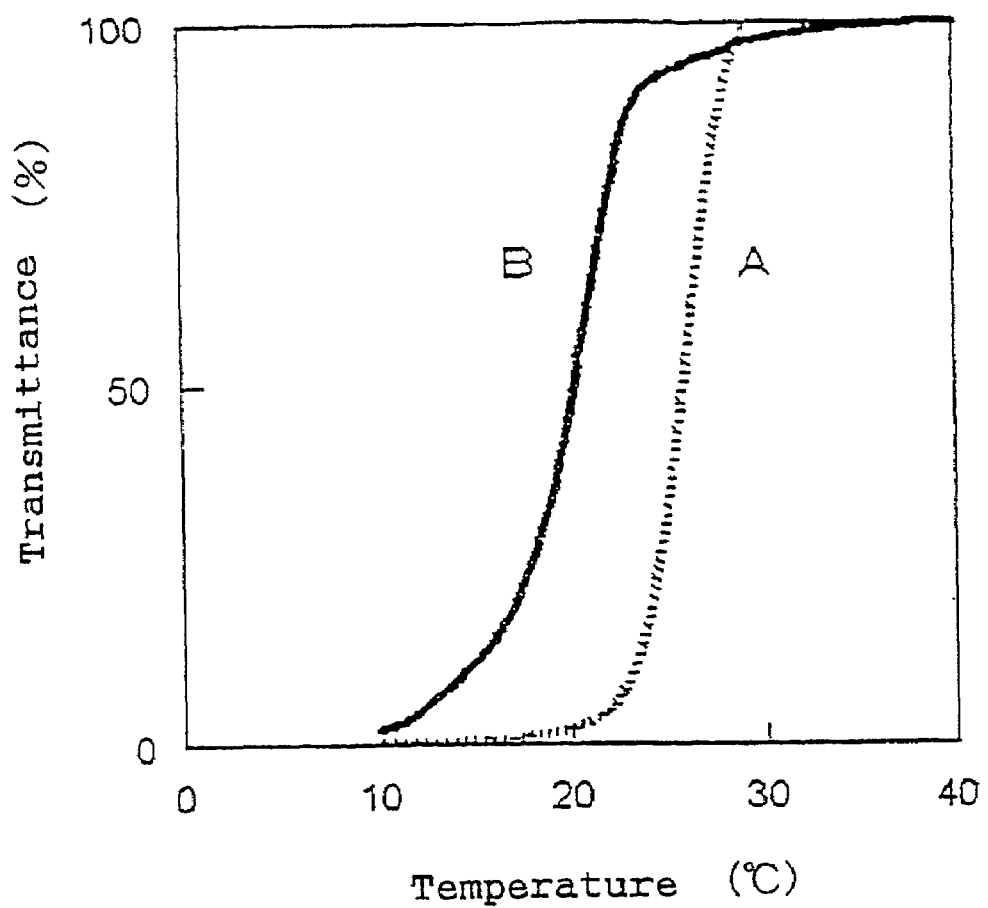
FIG. 15 provides a graph showing that the temperature-responsiveness of poly(acrylamide-co-3-acrylamide acetanilide) can be controlled depending on salt concentration obtained in Example E4.

This copolymer was dissolved in water and a 300 mM aqueous solution of sodium chloride each to give a concentration of 1% by weight. Then changes in transmittance with temperature change were monitored at 500 nm by using a spectrophotometer. FIG. 13 shows the results. In the aqueous solution, the UCST of this copolymer was 25° C. In the 300 mM aqueous sodium chloride solution, the UCST was lowered to 20° C. Thus, it was found that the temperature-responsiveness could be controlled depending on salt concentration (FIG. 15).

INDUSTRIAL APPLICABILITY

The separation method with the use of the separatory material according to the present invention has the following advantages.

1) It is possible to obtain a heat-responsive polymer having a larger side chain than those in the conventional heat-responsive polymers typified by the amide or ester type polymers.

2) The carbon atom number design and the cloud point can be arbitrarily controlled by appropriately combining alkyl groups in the side chain.

3) Thus, bioengineering products (proteins, etc.) having various polarities can be separated and purified.

4) The cloud point and the polarity of a polymeric compound can be arbitrarily controlled by appropriately combining two alkyl groups in the side chain.

In addition, the present invention can provide a temperature-responsive polymer compound the temperature-responsiveness of which can be easily controlled by changing the composition or functional groups of monomers constituting said polymer compound, the molecular weight of said polymer compound or the concentration of said polymer compound in a solution. Further, the present invention can provide a temperature-responsive polymer compound having an aromatic ring and being expected as exerting a high hydrophobicity or an electronic interaction which cannot be achieved by the existing temperature-responsive polymer compounds. Thus, it is expected that the present invention can largely contribute to the development of various temperature-responsive polymer compounds as well as to the development of adsorption and separation materials containing these temperature-responsive polymer compounds.

Furthermore, the present invention makes it possible to synthesize a heat-responsive polymer which contains a large amount of hydroxyl groups and has a highly hydrophobic nature, compared with the conventional amide-type heat-responsive polymers. Accordingly, the polarity and the hydrogen bonding properties can be controlled over a wide range. Sine the polarity and the hydrogen bonding properties vary depending on the molecular weight, concentration, density, etc. of the polymer, it is expected that the polymer compound of the present invention is usable in the separation, adsorption and release of substance including bioengineering products.

The present invention also makes it possible to control the expression of the UCST and the LCST of a polymer in an aqueous solution depending on the polymer composition. It also makes it possible to express the UCST or the LCST by changing the salt concentration or molecular weight. Moreover, it is found that the expression of the UCST and the LCST can be controlled. At the same time, the hydrophobic nature and the hydrogen-bonding properties of the polymer in an aqueous solution system can be controlled. Taking these effects into consideration, it is expected that the present invention largely contributes to the development of techniques for separating, adsorbing and releasing substances with the use of temperature-responsive polymer compounds.

What is claimed is:

1. A polymer compound comprising a structure selected from the group consisting of:

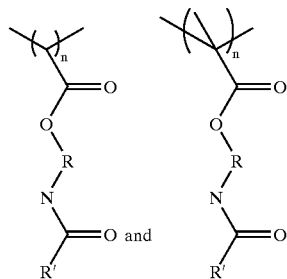

wherein:
R is a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms;

R' is a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and n is an integer of 2 or greater, wherein said polymer has acid amide bonds at two or more sites in the polymer chain.

2. A polymer material comprising a structure selected from the group consisting of:

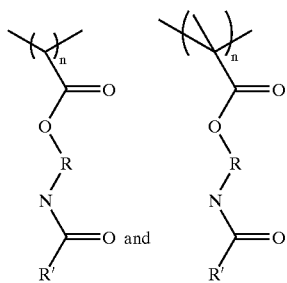
and
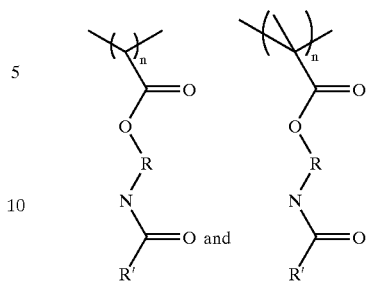
and wherein:
- R is a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms;
- R' is a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more acid amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and
- n is an integer of 2 or greater, wherein said polymer has acid amide bonds at two or more sites in the polymer chain.

3. A material for separating or absorbing biological samples comprising a structure selected from the group consisting of:

wherein:
- R is a linear or branched divalent aliphatic hydrocarbon group having 1 to 8 carbon atoms, a divalent alicyclic hydrocarbon group having 3 to 8 carbon atoms, or a divalent aromatic hydrocarbon group having 6 to 14 carbon atoms;
- R' is a linear or branched aliphatic hydrocarbon group having 1 to 8 carbon atoms, a linear or branched aliphatic hydrocarbon group having one or more hydroxyl groups and 1 to 8 carbon atoms, a linear or branched aliphatic hydrocarbon group having one or more add amide bonds and/or ester bonds and 2 to 9 carbon atoms, or a linear or branched aliphatic hydrocarbon group having one or more acid amide bonds and/or ester bonds, one or more hydroxyl groups and 3 to 9 carbon atoms; and
- n is an integer of 2 or greater, wherein said polymer has acid amide bonds at two or more sites in the polymer chain.

* * * * *